(12) United States Patent
Kikitsu et al.

(10) Patent No.: US 11,402,441 B2
(45) Date of Patent: Aug. 2, 2022

(54) MAGNETIC SENSOR AND INSPECTION DEVICE

(71) Applicant: KABUSHIKI KAISHA TOSHIBA, Tokyo (JP)

(72) Inventors: Akira Kikitsu, Kanagawa (JP); Satoshi Shirotori, Kanagawa (JP); Hitoshi Iwasaki, Tokyo (JP); Yoshihiro Higashi, Ishikawa (JP); Yoshinari Kurosaki, Kanagawa (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 0 days.

(21) Appl. No.: 17/177,014

(22) Filed: Feb. 16, 2021

(65) Prior Publication Data
US 2022/0065955 A1   Mar. 3, 2022

(30) Foreign Application Priority Data
Aug. 25, 2020   (JP) .............................. JP2020-141944

(51) Int. Cl.
| | | |
|---|---|---|
| *G01R 33/09* | (2006.01) | |
| *G01R 15/20* | (2006.01) | |
| *G01R 19/00* | (2006.01) | |
| *G01R 31/382* | (2019.01) | |
| *A61B 5/245* | (2021.01) | |

(52) U.S. Cl.
CPC ......... *G01R 33/093* (2013.01); *G01R 15/205* (2013.01); *G01R 19/0092* (2013.01); *G01R 31/382* (2019.01); *A61B 5/245* (2021.01)

(58) Field of Classification Search
CPC . G01R 33/093; G01R 19/0092; G01R 15/205
See application file for complete search history.

(56) References Cited

U.S. PATENT DOCUMENTS

2017/0285076 A1*  10/2017  Okuyama ............ G01R 33/093
2019/0293735 A1   9/2019  Ushioda et al.
2019/0307336 A1   10/2019  Fujii et al.
(Continued)

FOREIGN PATENT DOCUMENTS

JP   WO 2017/204151 A1   11/2017
JP   2018-102781 A       7/2018
(Continued)

*Primary Examiner* — Dominic E Hawkins
(74) *Attorney, Agent, or Firm* — Finnegan, Henderson, Farabow, Garrett & Dunner L.L.P.

(57) ABSTRACT

According to one embodiment, a magnetic sensor includes a first element part. The first element part includes a first magnetic element, a first conductive member, a first magnetic member, and a second magnetic member. The first magnetic element includes a first magnetic layer, a first counter magnetic layer, and a first nonmagnetic layer provided between the first magnetic layer and the first counter magnetic layer. A direction from the first magnetic layer toward the first counter magnetic layer is along a first direction. The second magnetic member is separated from the first magnetic member along a second direction crossing the first direction. The first magnetic element includes a first element region, a first other-element region, and a first intermediate element region. The first magnetic member includes a first partial surface and a second partial surface.

20 Claims, 15 Drawing Sheets

(56) References Cited

U.S. PATENT DOCUMENTS

2019/0369172 A1 12/2019 Kikitsu et al.
2020/0319269 A1* 10/2020 Shirotori ............ G01R 33/0011

FOREIGN PATENT DOCUMENTS

| JP | 2019-207167 A | 12/2019 |
| WO | WO 2019/238933 A1 | 12/2019 |
| WO | WO 2019/239933 A1 | 12/2019 |

* cited by examiner

Hsig=0

+Hsig

-Hsig

MAGNETIC SENSOR AND INSPECTION DEVICE

CROSS-REFERENCE TO RELATED APPLICATIONS

This application is based upon and claims the benefit of priority from Japanese Patent Application No. 2020-141944, filed on Aug. 25, 2020; the entire contents of which are incorporated herein by reference.

FIELD

Embodiments described herein relate generally to a magnetic sensor and an inspection device.

BACKGROUND

There is a magnetic sensor that uses a magnetic layer. There is an inspection device that uses a magnetic sensor. It is desirable to increase the sensitivity of the magnetic sensor.

DETAILED DESCRIPTION

Figure 1A:
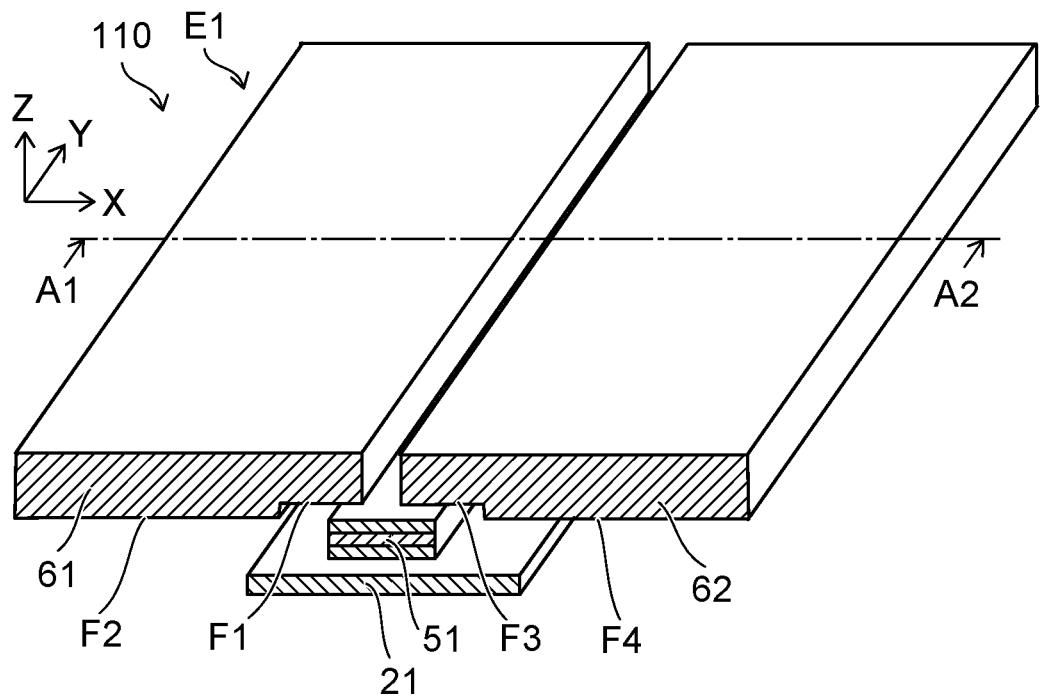
FIGS. 1A and 1B are schematic views illustrating a magnetic sensor according to a first embodiment.

According to one embodiment, a magnetic sensor includes a first element part. The first element part includes a first magnetic element, a first conductive member, a first magnetic member, and a second magnetic member. The first magnetic element includes a first magnetic layer, a first counter magnetic layer, and a first nonmagnetic layer provided between the first magnetic layer and the first counter magnetic layer. A direction from the first magnetic layer toward the first counter magnetic layer is along a first direction. The second magnetic member is separated from the first magnetic member along a second direction crossing the first direction. The first magnetic element includes a first element region, a first other-element region, and a first intermediate element region. The first element region is between a portion of the first conductive member and a portion of the first magnetic member in the first direction. The first other-element region is between the second magnetic member and an other portion of the first conductive member in the first direction. The first intermediate element region is between the first element region and the first other-element region in the second direction. The first intermediate element region overlaps a region between the first magnetic member and the second magnetic member in the first direction. The first magnetic member includes a first partial surface and a second partial surface. The first partial surface faces the first element region in the first direction. A position in the second direction of the first partial surface is between a position in the second direction of the second partial surface and a position in the second direction of the second magnetic member. A position in the first direction of the second partial surface is between a position in the first direction of the first conductive member and a position in the first direction of the first partial surface.

According to one embodiment, an inspection device includes the magnetic sensor described above, and a processor processing an output signal obtained from the magnetic sensor.

Various embodiments are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

Figure 1B:
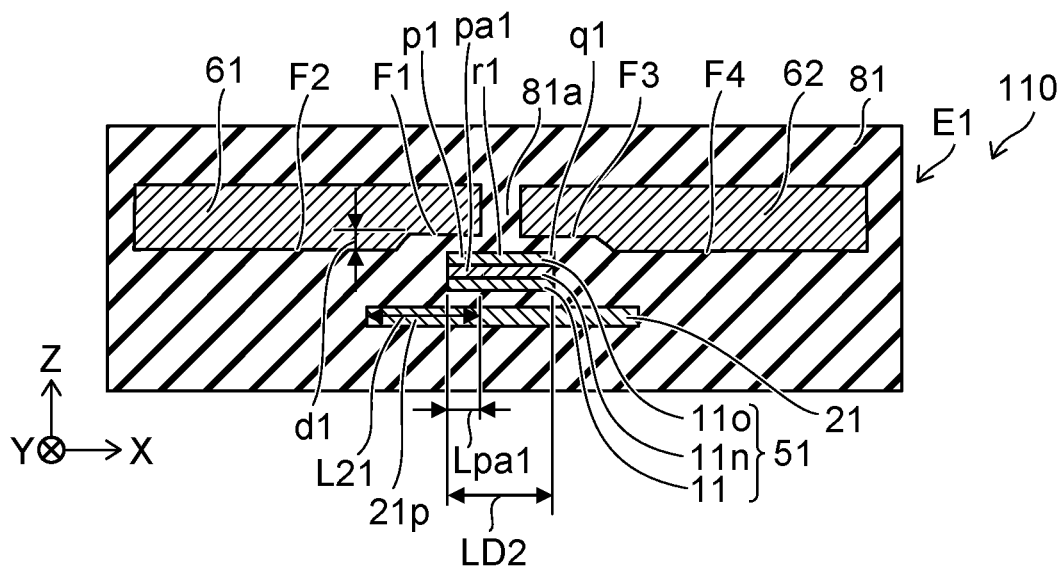

FIGS. 1A and 1B are schematic views illustrating a magnetic sensor according to a first embodiment.

FIG. 1A is a perspective view. FIG. 1B is a line A1-A2 cross-sectional view of FIG. 1A.

As shown in FIGS. 1A and 1B, the magnetic sensor 110 according to the embodiment includes a first element part E1. The first element part E1 includes a first magnetic element 51, a first conductive member 21, a first magnetic member 61, and a second magnetic member 62.

The first magnetic element 51 includes a first magnetic layer 11, a first counter magnetic layer 11o, and a first nonmagnetic layer 11n. The first nonmagnetic layer 11n is located between the first magnetic layer 11 and the first counter magnetic layer 11o. The first nonmagnetic layer 11n is, for example, a nonmagnetic conductive layer (e.g., a metal layer). The direction from the first magnetic layer 11 toward the first counter magnetic layer 11o is along a first direction.

The first direction is taken as a Z-axis direction. One direction perpendicular to the Z-axis direction is taken as an X-axis direction. A direction perpendicular to the Z-axis direction and the X-axis direction is taken as a Y-axis direction.

The second magnetic member 62 is separated from the first magnetic member 61 along a second direction. The second direction crosses the first direction. The second direction is, for example, the X-axis direction.

As shown in FIG. 1B, the first magnetic element 51 includes a first element region p1, a first other-element region q1, and a first intermediate element region r1. The first element region p1 is between a portion of the first conductive member 21 and a portion of the first magnetic member 61 in the first direction (the Z-axis direction). The first other-element region q1 is between the second magnetic member 62 and another portion of the first conductive member 21 in the first direction. The first intermediate element region r1 is between the first element region p1 and the first other-element region q1 in the second direction (e.g., the X-axis direction). The first intermediate element region r1 overlaps a region 81a between the first magnetic member 61 and the second magnetic member 62 in the first direction (the Z-axis direction).

An insulating member 81 is provided in the example. The insulating member 81 is located around the first magnetic element 51, the first conductive member 21, the first magnetic member 61, and the second magnetic member 62. A portion of the insulating member 81 is located between the first magnetic element 51, the first conductive member 21, the first magnetic member 61, and the second magnetic member 62. The region 81a may be, for example, a portion of the insulating member 81. The insulating member 81 is not illustrated in FIG. 1A.

According to the embodiment, the electrical resistance of the first magnetic element 51 changes according to the change of an external magnetic field. The first magnetic element 51 is, for example, a GMR (Giant Magneto-Resistance) element. For example, the electrical resistance of the first magnetic element 51 changes with respect to a magnetic field including a component in the second direction (the X-axis direction).

The external magnetic field (e.g., the magnetic field to be detected) is concentrated by the first and second magnetic members 61 and 62. The concentrated magnetic field is applied to the first magnetic element 51. For example, the first magnetic member 61 and the second magnetic member 62 function as MFCs (Magnetic Flux Concentrators).

As shown in FIG. 1B, the first magnetic member 61 includes a first partial surface F1 and a second partial surface F2. The first partial surface F1 faces the first element region p1 in the first direction (the Z-axis direction). The position in the second direction (the X-axis direction) of the first partial surface F1 is between the position in the second direction of the second partial surface F2 and the position in the second direction of the second magnetic member 62. The first partial surface F1 is, for example, the surface at the inner side. The second partial surface F2 is, for example, the surface at the outer side. The position in the first direction (the Z-axis direction) of the second partial surface F2 is between the position in the first direction of the first conductive member 21 and the position in the first direction of the first partial surface F1.

For example, the first magnetic element 51 is located on the first conductive member 21. The first partial surface F1 of the first magnetic member 61 is located on the first magnetic element 51. The second partial surface F2 is lower than the first partial surface F1 in the first direction (the Z-axis direction).

For example, the magnetic field is applied to the first magnetic element 51 with high efficiency by the first magnetic member 61 having such a shape. For example, the magnetic field to be detected is concentrated with high efficiency; and the concentrated magnetic field is applied to the first magnetic element 51. As described below, a current is supplied to the first conductive member 21. A current magnetic field is generated thereby. For example, the current magnetic field due to the first conductive member 21 is applied to the first magnetic element 51 with high efficiency by the first magnetic member 61 having a shape such as that described above. As described below, the magnetic field to be detected can detect with high sensitivity by using the current magnetic field.

According to the embodiment, the magnetic field to be detected can detect with high sensitivity. According to the embodiment, a magnetic sensor can be provided in which the sensitivity can be increased.

As shown in FIG. 1B, the shape of the second magnetic member 62 may be similar to the shape of the first magnetic member 61. For example, the second magnetic member 62 includes a third partial surface F3 and a fourth partial surface F4. The third partial surface F3 faces the first other-element region q1 in the first direction (the Z-axis direction). The position in the second direction (the X-axis direction) of the third partial surface F3 is between the position in the second direction of the first magnetic member 61 and the position in the second direction of the fourth partial surface F4. The position in the first direction (the Z-axis direction) of the fourth partial surface F4 is between the position in the first direction of the first conductive member 21 and the position in the first direction of the third partial surface F3. The magnetic field is applied to the first magnetic element 51 with a higher efficiency by such a second magnetic member 62.

According to the embodiment, for example, the position in the X-axis direction of at least a portion of the first magnetic element 51 is between the position in the X-axis direction of at least a portion of the first magnetic member 61 and the position in the X-axis direction of at least a portion of the second magnetic member 62. Due to such an arrangement, the electrical resistance of the first magnetic element 51 efficiently changes with respect to the magnetic field including a component in the second direction (the X-axis direction).

For example, the first magnetic element 51 may be between the first magnetic member 61 and the second magnetic member 62 in the X-axis direction. For example, the first magnetic element 51 may be at the same height (in the Z-axis direction) as the first and second magnetic members 61 and 62. In such a case, the electrical resistance of the first magnetic element 51 efficiently changes with respect to the magnetic field including a component in the second direction (the X-axis direction).

As shown in FIG. 1B, the first magnetic member 61 and the second magnetic member 62 may be higher than the first magnetic element 51 in the Z-axis direction. It was found that in such a case as well, the electrical resistance of the first magnetic element 51 efficiently changes with respect to the magnetic field including a component in the second direction (the X-axis direction).

For example, the magnetic field concentrates at the step between the first partial surface F1 and the second partial surface F2 of the first magnetic member 61; the concentrated magnetic field is applied to the first magnetic element 51; therefore, the electrical resistance of the first magnetic element 51 efficiently changes with respect to the magnetic field including the X-axis direction component. For example, the magnetic field concentrates at the step between the third partial surface F3 and the fourth partial surface F4 of the second magnetic member 62; the concentrated magnetic field is applied to the first magnetic element 51; therefore, the electrical resistance of the first magnetic element 51 efficiently changes with respect to the magnetic field including the X-axis direction component. By providing such partial surfaces at different heights, the concentrated magnetic field can be applied more efficiently to the first magnetic element 51 even when the first magnetic member 61 and the second magnetic member 62 are higher than the first magnetic element 51.

For example, a structure in which the first magnetic member 61 and the second magnetic member 62 are higher than the first magnetic element 51 in the first direction (the Z-axis direction) is easier to manufacture than a structure in which the first magnetic element 51 is between the first magnetic member 61 and the second magnetic member 62.

By setting the first partial surface F1 that forms the step to overlap the first magnetic element 51 in the Z-axis direction, the magnetic field that includes the X-axis direction component can be more efficiently concentrated and applied to the first magnetic element 51. By setting the third partial surface F3 that forms the step to overlap the first magnetic element 51 in the Z-axis direction, the magnetic field that includes the X-axis direction component can be more efficiently concentrated and applied to the first magnetic element 51.

For example, the external magnetic field that includes the X-axis direction component and the current magnetic field that includes the X-axis direction component are concentrated to become a magnetic field from the first magnetic member 61 toward the second magnetic member 62 or a magnetic field from the second magnetic member 62 toward the first magnetic member 61 that is efficiently applied to the first magnetic element 51.

As shown in FIG. 1B, a portion of the first conductive member 21 may overlap at least a portion of the second partial surface F2 in the first direction (the Z-axis direction). Thereby, the current magnetic field from the first conductive member 21 can be concentrated with a higher efficiency and applied to the first magnetic element 51.

Another portion of the first conductive member 21 may overlap at least a portion of the second partial surface F2 in the first direction (the Z-axis direction). Thereby, the current magnetic field from the first conductive member 21 can be concentrated with a higher efficiency and applied to the first magnetic element 51.

Examples of simulation results of characteristics will now be described.

FIGS. 2A to 2G are schematic cross-sectional views showing models of the simulation.

Figure 2A:
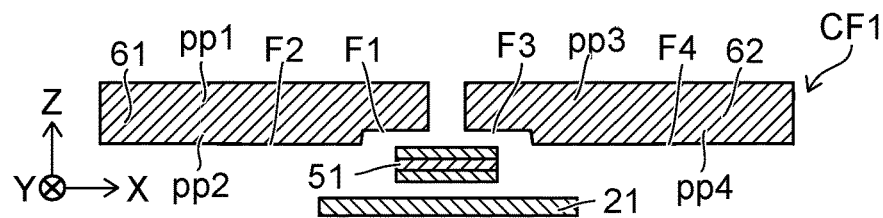
FIGS. 2A to 2G are schematic cross-sectional views showing models of the simulation.
Figure 2B:
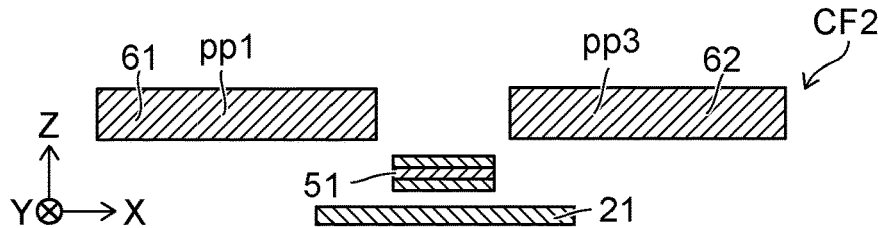
Figure 2C:
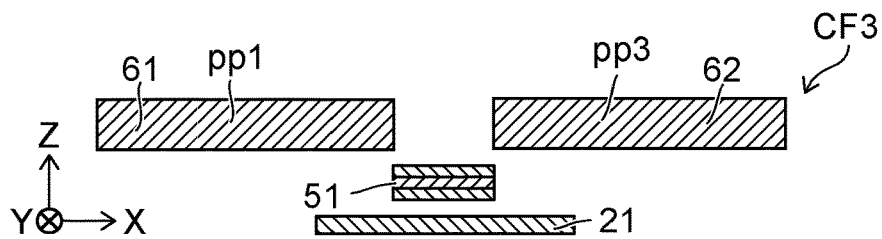
Figure 2D:
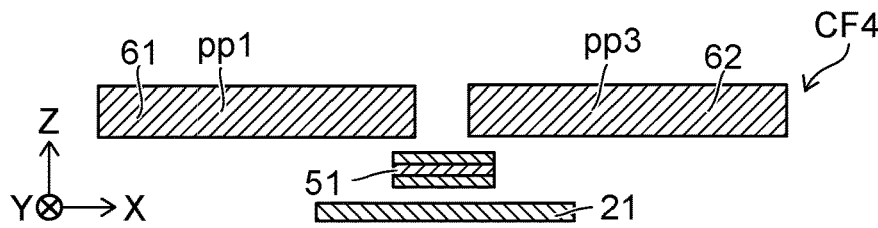
Figure 2E:
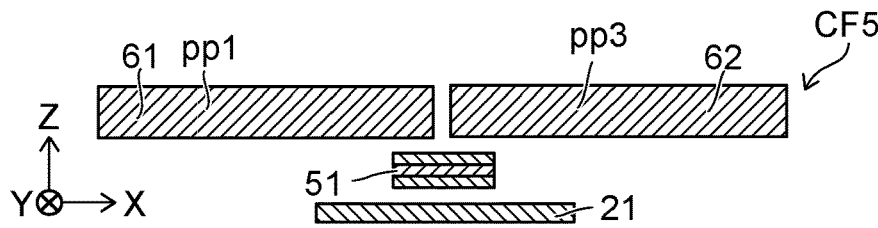

In a first configuration CF1 shown in FIG. 2A, the first partial surface F1 and the second partial surface F2 are provided in the first magnetic member 61; and the third partial surface F3 and the fourth partial surface F4 are provided in the second magnetic member 62. The difference between the height (the position in the Z-axis direction) of the first partial surface F1 and the height (the position in the Z-axis direction) of the second partial surface F2 (the height of the step) is 350 nm. The difference corresponds to a distance between the first partial surface F1 and the second partial surface F2. The difference between the height (the position in the Z-axis direction) of the third partial surface F3 and the height (the position in the Z-axis direction) of the fourth partial surface F4 (the height of the step) is 350 nm.

The distance (the gap) along the X-axis direction between the first magnetic member 61 and the second magnetic member 62 is 3 µm. In the first configuration CF1, the upper portion of the first magnetic member 61 is taken as a portion pp1; and the lower portion of the first magnetic member 61 is taken as a portion pp2. In the first configuration CF1, the upper portion of the second magnetic member 62 is taken as a portion pp3; and the lower portion of the second magnetic member 62 is taken as a portion pp4. The length in the X-axis direction of the first partial surface F1 is 10 µm; and the length in the X-axis direction of the third partial surface F3 is 10 µm. The length (a second-direction length LD2) along the X-axis direction of the first magnetic element is 5 µm.

In second to fifth configurations CF2 to CF5 as shown in FIGS. 2B to 2E, the portion pp1 is provided in the first magnetic member 61, but the portion pp2 is not provided in the first magnetic member 61. The portion pp3 is provided in the second magnetic member 62, but the portion pp4 is not provided in the second magnetic member 62. In the second configuration CF2, the distance (the gap) along the X-axis direction between the first magnetic member 61 and the second magnetic member 62 is 7 µm. In the third configuration CF3, the distance (the gap) along the X-axis direction between the first magnetic member 61 and the second magnetic member 62 is 5 µm. In the fourth configuration CF4, the distance (the gap) along the X-axis direction between the first magnetic member 61 and the second magnetic member 62 is 3 µm. In the fifth configuration CF5, the distance (the gap) along the X-axis direction between the first magnetic member 61 and the second magnetic member 62 is 1 µm.

Figure 2F:
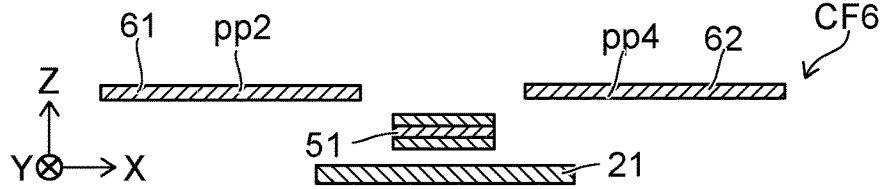

In a sixth configuration CF6 as shown in FIG. 2F, the portion pp2 is provided in the first magnetic member 61, but the portion pp1 is not provided in the first magnetic member 61. The portion pp4 is provided in the second magnetic member 62, but the portion pp3 is not provided in the second magnetic member 62. The distance between the portion pp2 and the portion pp4 is 23 µm.

Figure 2G:
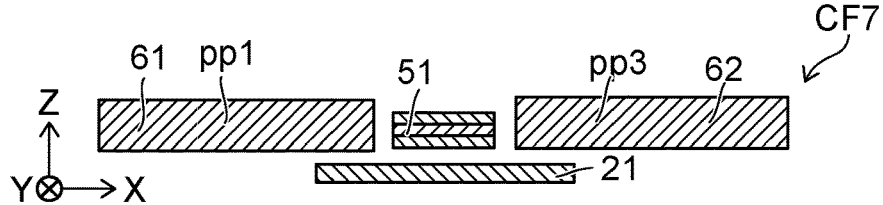

In a seventh configuration CF7 as shown in FIG. 2G, a portion that corresponds to the portion pp1 is provided, but a portion that corresponds to the portion pp2 is not provided. In the second magnetic member 62, a portion that corresponds to the portion pp3 is provided, but a portion that corresponds to the portion pp4 is not provided. The distance between the portion corresponding to the portion pp1 and the portion corresponding to the portion pp3 is 5.2 µm.

In the simulation, magnetic properties of NiFe are used as those of the first and second magnetic members 61 and 62. magnetic properties of FeCo are used as those of the first magnetic layer 11 and the first counter magnetic layer 11o. Magnetic properties of Cu are used as those of the first conductive member 21.

Figure 3A:
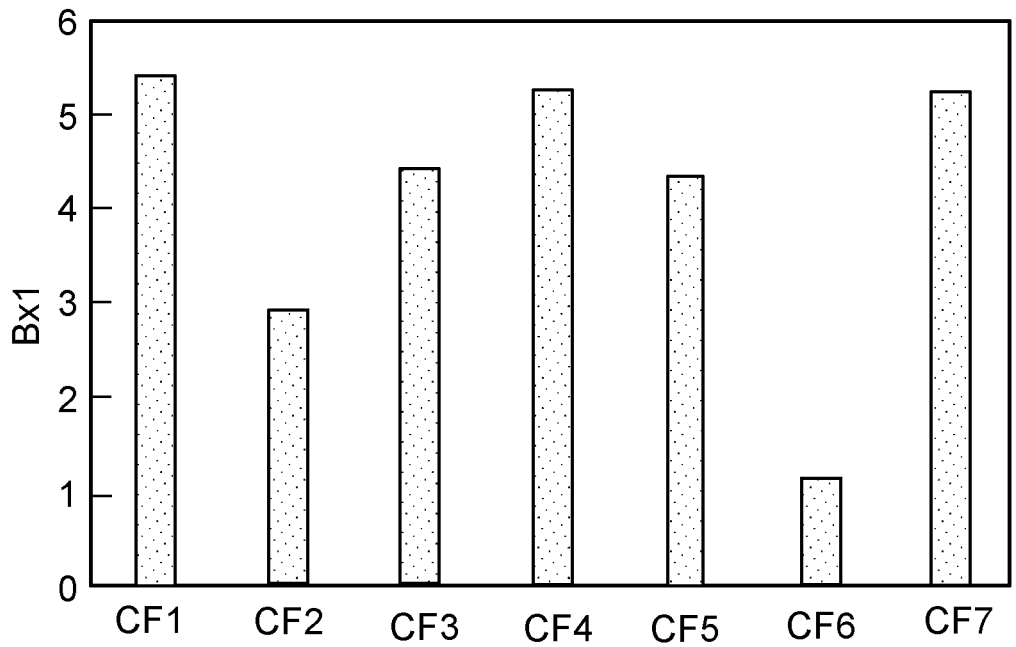
FIGS. 3A and 3B are graphs illustrating results of the simulation.
Figure 3B:
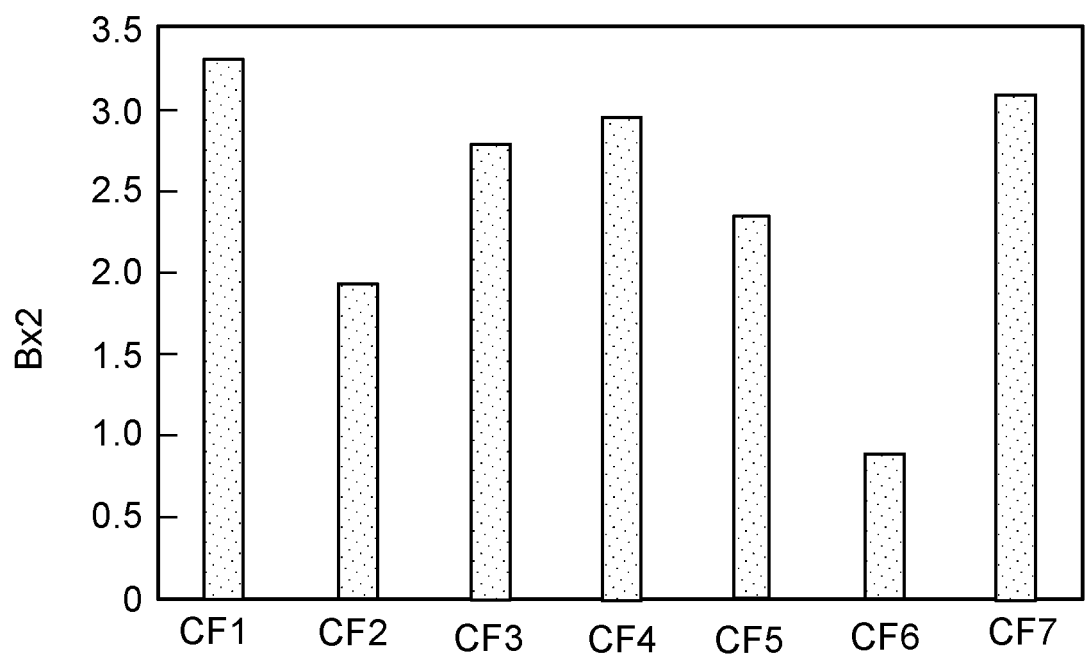

FIGS. 3A and 3B are graphs illustrating results of the simulation.

FIG. 3A shows the magnetic flux density at the position of the first magnetic element 51 when the external magnetic field is applied for models such as those described above. The vertical axis of FIG. 3A is an average magnetic flux density Bx1 in the X-axis direction (a normalized value). FIG. 3B shows the magnetic flux density at the position of the first magnetic element 51 when the current is supplied to the first conductive member 21 for models such as those described above. The vertical axis of FIG. 3B is an average magnetic flux density Bx2 in the X-axis direction (a normalized value).

As shown in FIG. 3A, the magnetic flux density Bx1 is high for the first configuration CF1. Comparing the second to fourth configurations CF2 to CF4, the magnetic flux density Bx1 is high when the gap is short. However, the magnetic flux density Bx1 is low when the gap is excessively short as in the fifth configuration CF5. The magnetic flux density Bx1 is low for the sixth configuration CF6. The magnetic flux density Bx1 of the first configuration CF1 is higher than the magnetic flux density Bx1 of the seventh configuration CF7. According to the first configuration CF1, the first magnetic member 61 and the second magnetic member 62 are located higher than the first magnetic element 51 in the Z-axis direction; the manufacturing is easy; and a high magnetic flux density B1 is obtained.

As shown in FIG. 3B, the magnetic flux density Bx2 is high for the first configuration CF1. Comparing the second to fourth configurations CF2 to CF4, the magnetic flux density Bx2 is high when the gap is short. However, the magnetic flux density Bx2 is low when the gap is excessively short as in the fifth configuration CF5. The magnetic flux density Bx2 is low in the sixth configuration CF6. The magnetic flux density Bx2 of the first configuration CF1 is higher than the magnetic flux density Bx2 of the seventh configuration CF7. According to the first configuration CF1, the first magnetic member 61 and the second magnetic member 62 are located higher than the first magnetic element 51 in the Z-axis direction; the manufacturing is easy; and a high magnetic flux density B2 is obtained.

As shown in FIG. 1B, the distance along the first direction between the position of the first partial surface F1 and the position in the first direction of the second partial surface F2 is taken as a distance dl. According to the embodiment, it is favorable for the first distance dl to be, for example, not less than 100 nm. By setting the first distance dl to be not less than 100 nm, for example, the magnetic field from the outside (the magnetic field to be detected and the current magnetic field due to the first conductive member 21) are efficiently applied to the first magnetic element 51. The distance dl may be not less than 50 nm. The distance dl may be not more than 3000 nm.

As shown in FIG. 1B, the first element region p1 includes a portion pa1 facing the first partial surface F1 in the first direction (the Z-axis direction). The portion pa1 overlaps the first partial surface F1 in the first direction. It is favorable for a length Lpa1 along the second direction (the X-axis direction) of the portion pa1 to be not less than 0.1 times and not more than 0.9 times the length (the second-direction length LD2) along the second direction of the first magnetic element 51. Thereby, the concentrated magnetic field is more efficiently applied to the first magnetic element 51.

As shown in FIG. 1B, the first conductive member 21 includes a portion 21p overlapping the first magnetic member 61 in the first direction (the Z-axis direction). For example, it is favorable for a length L21 along the second direction (the X-axis direction) of the portion 21p to be not less than 2 times the length (the second-direction length LD2) along the second direction (e.g., the X-axis direction) of the first magnetic element 51. Thereby, the component along the X-axis direction of the current magnetic field due to the first conductive member 21 is more efficiently applied to the first magnetic element 51.

Figure 4A:
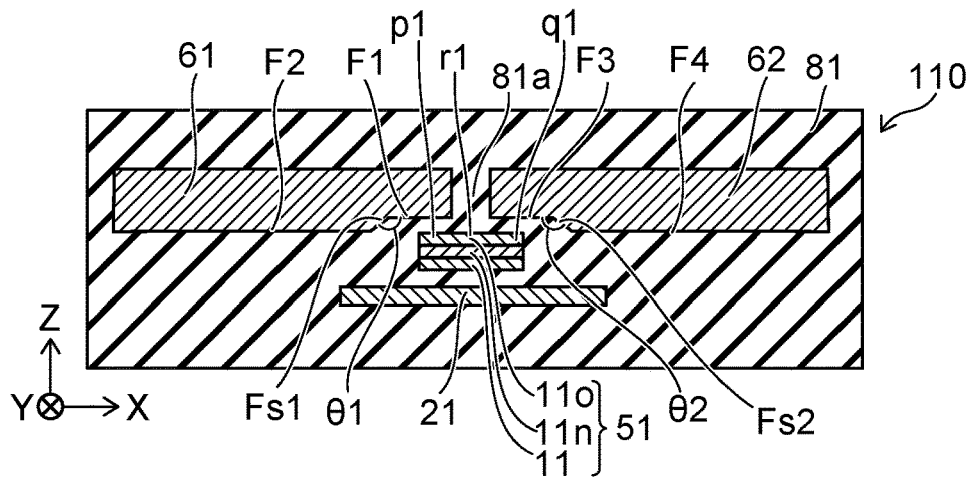
FIGS. 4A to 4C are schematic cross-sectional views illustrating magnetic sensors according to the first embodiment.
Figure 4B:
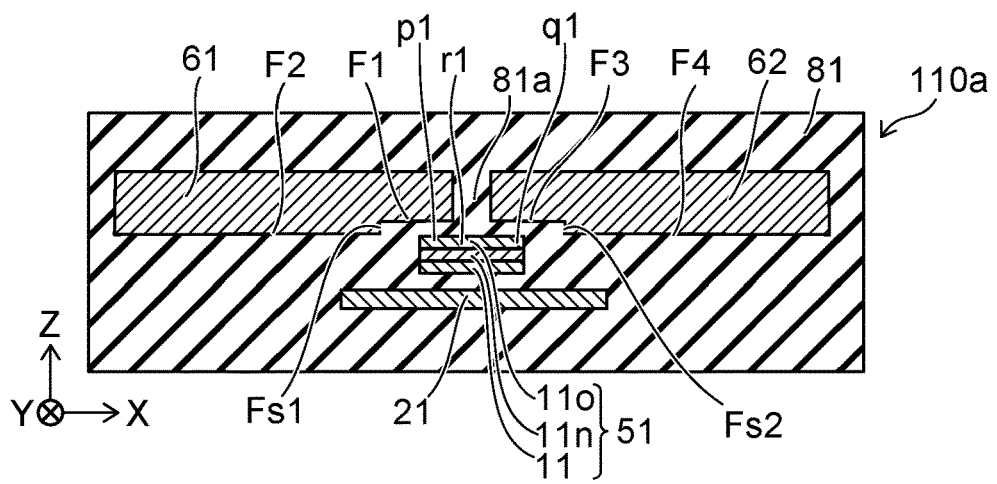
Figure 4C:
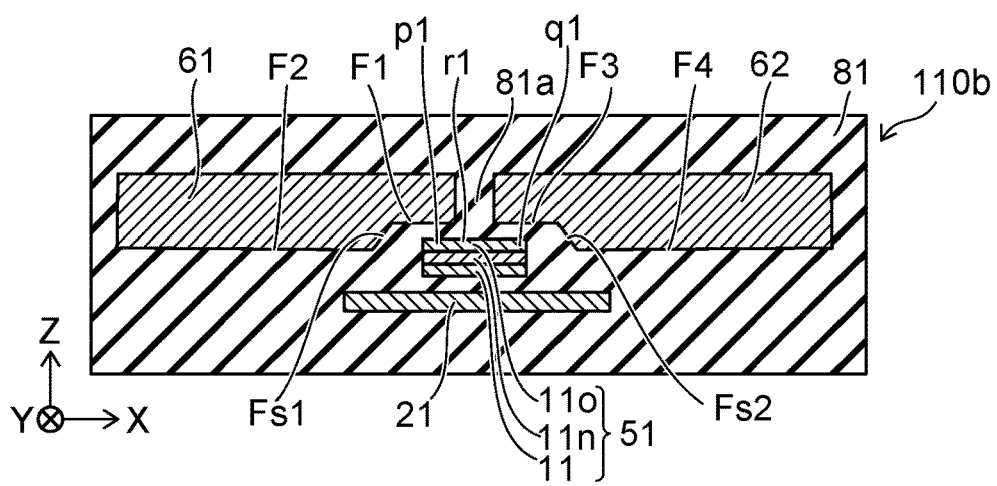

FIGS. 4A to 4C are schematic cross-sectional views illustrating magnetic sensors according to the first embodiment. FIGS. 4A to 4C are cross-sectional views corresponding to a line A1-A2 cross section of FIG. 1A. In the magnetic sensor 110 as shown in FIG. 4A, the first magnetic member 61 includes a first partial side surface Fs1 between the first partial surface F1 and the second partial surface F2. The first partial side surface Fs1 may be oblique to the first partial surface F1. For example, an angle θ1 between the first partial side surface Fs1 and the first partial surface F1 is not less than 95 degrees and not more than 175 degrees. By setting the first partial side surface Fs1 to be oblique, the magnetic field from the first magnetic member 61 is efficiently oriented from the first partial side surface Fs1 toward the first magnetic element 51. For example, the magnetic field efficiently enters the first magnetic member 61 from the first partial side surface Fs1; and the magnetic field efficiently passes through the first magnetic element 51.

For example, the second magnetic member 62 includes a second partial side surface Fs2 between the third partial surface F3 and the fourth partial surface F4. The second partial side surface Fs2 may be oblique to the third partial surface F3. For example, an angle θ2 between the second partial side surface Fs2 and the third partial surface F3 is not less than 95 degrees and not more than 175 degrees. By setting the second partial side surface Fs2 to be oblique, the magnetic field from the second magnetic member 62 is efficiently oriented from the second partial side surface Fs2 toward the first magnetic element 51. For example, the magnetic field efficiently enters the second magnetic member 62 from the second partial side surface Fs2; and the magnetic field efficiently passes through the first magnetic element 51.

As in a magnetic sensor 110a shown in FIG. 4B, the first partial side surface Fs1 may be substantially perpendicular to the first partial surface F1. The second partial side surface Fs2 may be substantially perpendicular to the third partial surface F3. As in a magnetic sensor 110b shown in FIG. 4C, at least a portion of the first magnetic element 51 may be between the second partial surface F2 and the fourth partial surface F4. In the magnetic sensors 110a and 110b as well, the magnetic field can be efficiently applied to the first magnetic element 51. A magnetic sensor can be provided in which the sensitivity can be increased.

According to the embodiment, the first magnetic layer 11 and the first counter magnetic layer 11o include, for example, Fe and Co. The first magnetic layer 11 and the first counter magnetic layer 11o include, for example, an FeCo alloy. For example, a high magnetoresistance ratio is obtained thereby. For example, the magnetization of the magnetic layer with respect to the magnetic field to be detected is more easily rotated. For example, good soft magnetic properties are obtained. For example, high sensitivity is obtained.

The first magnetic member 61 and the second magnetic member 62 include, for example, at least one selected from the group consisting of Fe, Co, and Ni. The first magnetic member 61 and the second magnetic member 62 include, for example, an alloy including at least two selected from the group consisting of Fe, Co, and Ni. For example, a high magnetic permeability is obtained. The current magnetic field and the magnetic field to be detected can be efficiently applied to the first magnetic element 51.

Figure 5A:
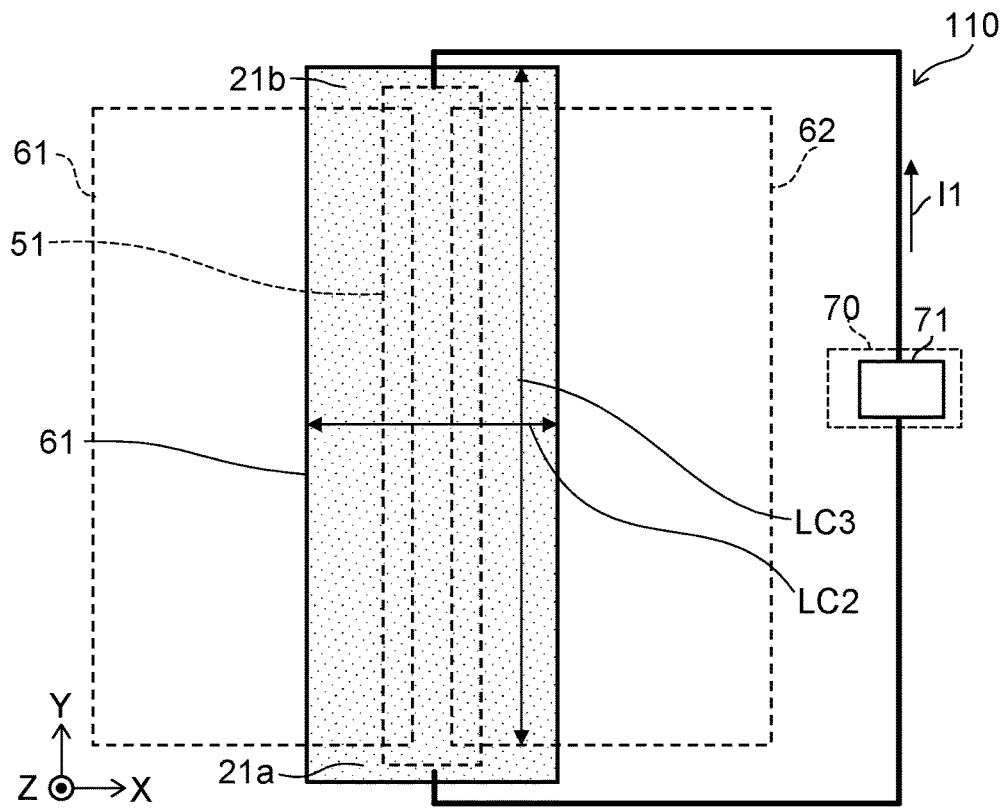
FIGS. 5A and 5B are schematic plan views illustrating the magnetic sensor according to the first embodiment.
Figure 5B:
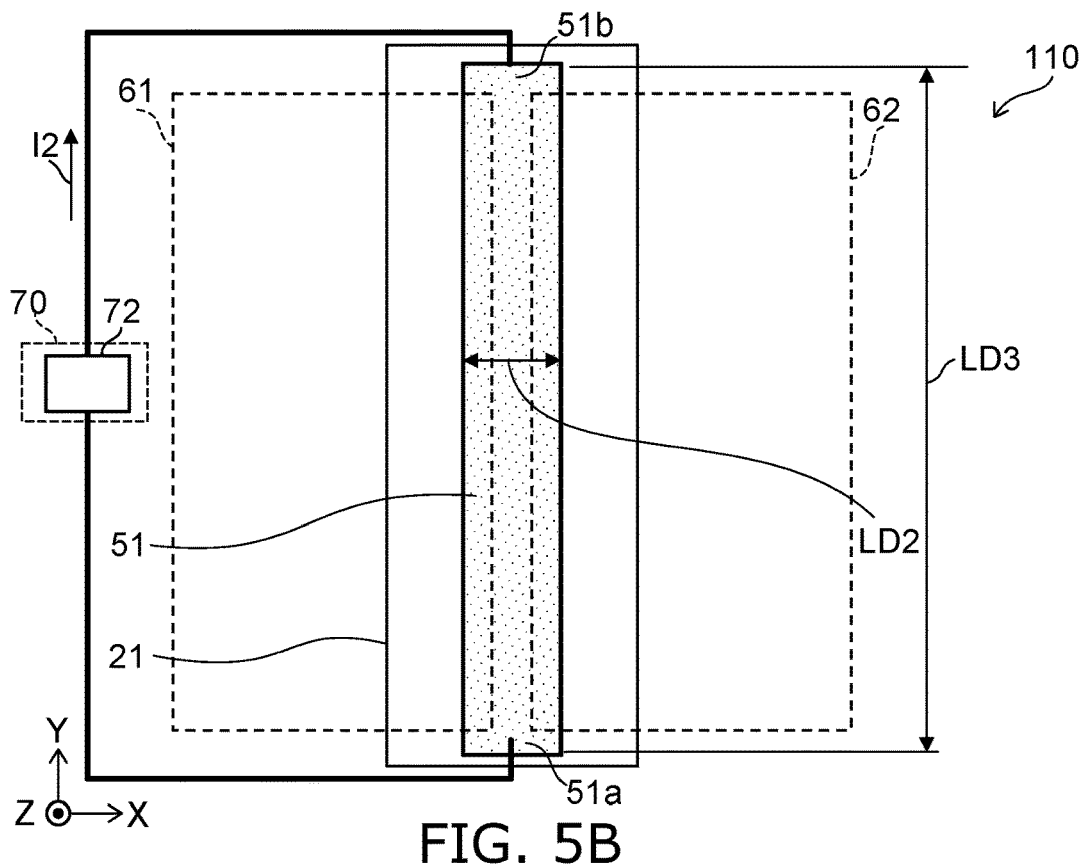

FIGS. 5A and 5B are schematic plan views illustrating the magnetic sensor according to the first embodiment. In these drawings, some of the components are not illustrated as appropriate for easier viewing of the drawings.

As shown in FIG. 5A, the first conductive member 21 has a length LC2 along the X-axis direction. The first conductive member 21 has a length LC3 along the Y-axis direction. The length LC3 is greater than the length LC2. For example, the length LC3 is not less than 5 times the length LC2. For example, the length LC3 may be not less than 10 times the length LC2. A current magnetic field is generated by supplying a current to the first conductive member 21. The current magnetic field that is generated from the first conductive member 21 having a shape such as that described above has an X-axis direction component. For example, the current magnetic field along the X-axis direction is efficiently applied to the first magnetic element 51.

As shown in FIG. 5A, the magnetic sensor 110 may further include a first circuit 71. The first circuit 71 may be included in a circuit part 70. The first conductive member 21 includes a first conductive portion 21a and a first other-conductive portion 21b. The direction from the first conductive portion 21a toward the first other-conductive portion 21b is along a third direction. The third direction crosses a plane including the first and second directions. The third direction is, for example, the Y-axis direction. The first circuit 71 is electrically connected to the first conductive portion 21a and the first other-conductive portion 21b. The first circuit 71 is configured to supply a first current I1 including the alternating current component between the first conductive portion 21a and the first other-conductive portion 21b.

The alternating current magnetic field due to the first current I1 includes an X-axis direction component. The alternating current magnetic field due to the first current I1 is along the X-axis direction. Such a current magnetic field is applied to the first magnetic element 51.

As shown in FIG. 5B, the first magnetic element 51 has the second-direction length LD2 along the second direction (e.g., the X-axis direction). The first magnetic element 51 has a third-direction length LD3 along the third direction. As described above, the third direction crosses a plane including the first and second directions. The third direction is, for example, the Y-axis direction. The third-direction length LD3 is greater than the second-direction length LD2. For example, the third-direction length LD3 is not less than 5 times the second-direction length LD2. For example, the third-direction length LD3 may be not less than 10 times the second-direction length LD2.

By setting the third-direction length LD3 to be greater than the second-direction length LD2, for example, the magnetization of the first magnetic layer 11 and the magnetization of the first counter magnetic layer 11o are easily aligned with the third direction (the Y-axis direction). For example, the resistance of the first magnetic element 51 changes as a substantially even function of the magnetic field from the outside.

For example, the first magnetic layer 11 is one of a free magnetic layer or a reference layer. For example, the first counter magnetic layer 11o is the other of the free magnetic layer or the reference layer.

As shown in FIG. 5B, the magnetic sensor 110 may include a second circuit 72. The second circuit 72 may be included in the circuit part 70. The first magnetic element 51 includes a first element portion 51a and a first other-element portion 51b. The direction from the first element portion 51a toward the first other-element portion 51b is along the third direction (e.g., the Y-axis direction). The second circuit 72 is electrically connected to the first element portion 51a and the first other-element portion 51b. The second circuit 72 is configured to supply a second current I2 between the first element portion 51a and the first other-element portion 51b. The second current I2 may be, for example, a direct current. For example, the electrical resistance of the first magnetic element 51 changes according to the external magnetic field. The change of the electrical resistance can be detected using the second current I2.

According to the embodiment, the electrical resistance of the first magnetic element 51 changes as a substantially even function of the external magnetic field. By supplying the first current I1 including the alternating current component to the first conductive member 21, the alternating current magnetic field that is generated is applied to the first magnetic element 51. By such a configuration, the magnetic field to be detected can be detected with high sensitivity.

An example of the change of the electrical resistance of the magnetic element will now be described.

Figure 6:
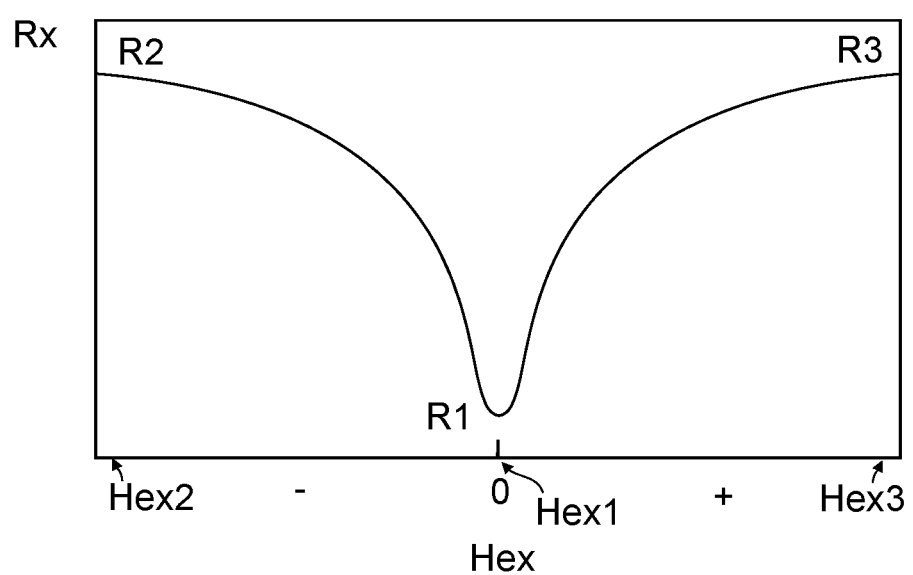
FIG. 6 is a graph illustrating a characteristic of the magnetic sensor according to the first embodiment.

FIG. 6 is a graph illustrating a characteristic of the magnetic sensor according to the first embodiment.

The horizontal axis of FIG. 6 is the intensity of an external magnetic field Hex applied to the first magnetic element 51. The vertical axis is an electrical resistance Rx of the first magnetic element 51. FIG. 6 corresponds to the R-H characteristic.

As shown in FIG. 6, the electrical resistance Rx has an even-function characteristic of the magnetic field (the external magnetic field Hex; e.g., a magnetic field in the X-axis direction) applied to the first magnetic element 51. For example, the electrical resistance Rx has a first value R1 when a first magnetic field Hex1 is applied to the first magnetic element 51. The electrical resistance Rx has a second value R2 when a second magnetic field Hex2 is applied to the first magnetic element 51. The electrical resistance Rx has a third value R3 when a third magnetic field Hex3 is applied to the first magnetic element 51. The absolute value of the first magnetic field Hex1 is less than the absolute value of the second magnetic field Hex2 and less than the absolute value of the third magnetic field Hex3. For example, the first magnetic field Hex1 is substantially 0. The orientation of the second magnetic field Hex2 is opposite to the orientation of the third magnetic field Hex3. The first value R1 is less than the second value R2 and less than the third value R3.

An example in which the first current I1 is an alternating current and substantially does not include a direct current component will now be described. The first current I1. (the alternating current) is supplied to the first conductive member 21; and the alternating current magnetic field due to the alternating current is applied to the first magnetic element 51. An example of the change of the electrical resistance Rx at this time will be described.

Figure 7A:
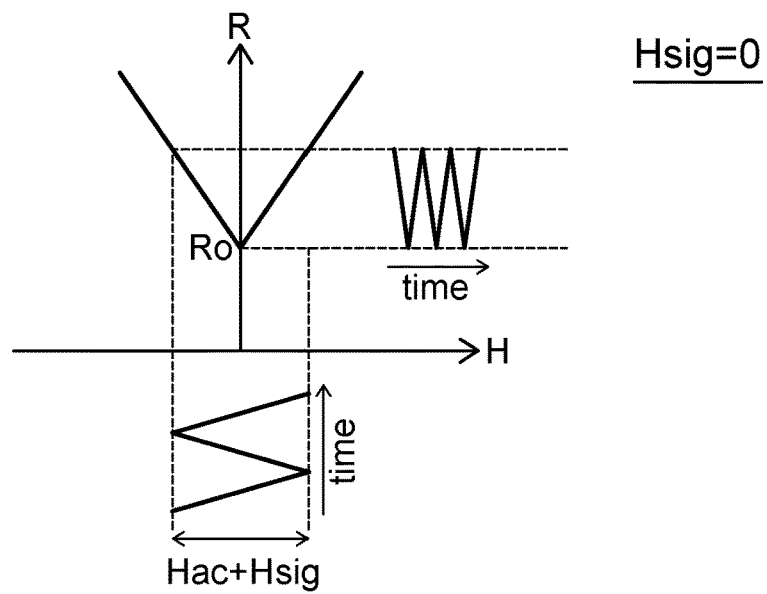
FIGS. 7A to 7C are graphs illustrating characteristics of the magnetic sensor according to the first embodiment.
Figure 7B:
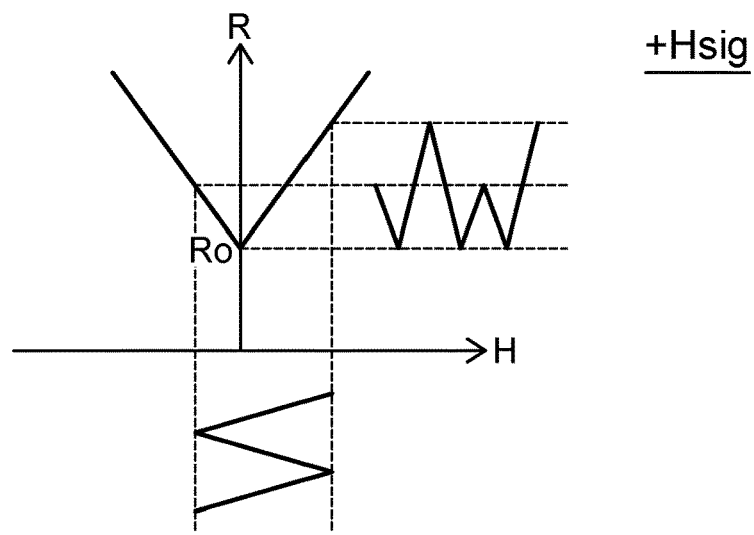
Figure 7C:
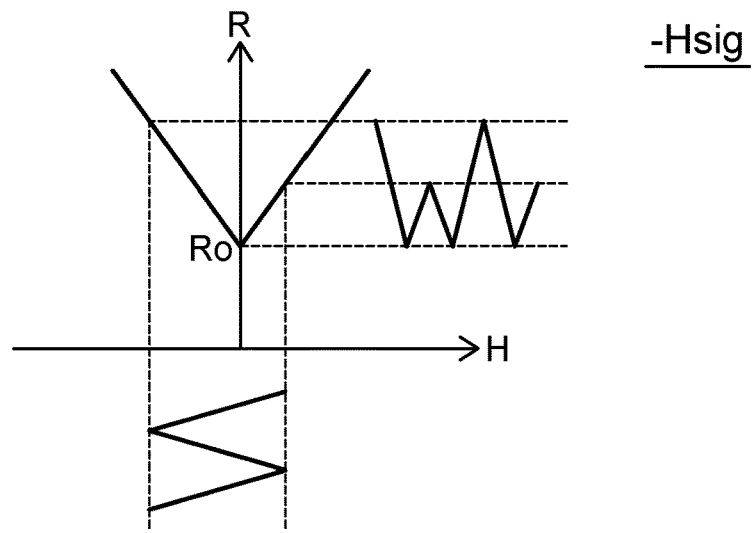

FIGS. 7A to 7C are graphs illustrating characteristics of the magnetic sensor according to the first embodiment.

FIG. 7A shows characteristics when a signal magnetic field Hsig (an external magnetic field) applied to the first magnetic element 51 is 0. FIG. 7B shows characteristics when the signal magnetic field Hsig is positive. FIG. 7C shows characteristics when the signal magnetic field Hsig is negative. These figures show the relationship between a magnetic field H and a resistance R (corresponding to the electrical resistance Rx).

As shown in FIG. 7A, when the signal magnetic field Hsig is 0, the resistance R has a characteristic that is symmetric with respect to the positive and negative magnetic field H. When an alternating current magnetic field Hac is zero, the resistance R is a low resistance Ro. For example, the magnetization of the free magnetic layer is rotated substantially identically to the positive and negative magnetic field H. Therefore, a symmetric resistance increase characteristic is obtained. The change in the resistance R with respect to the alternating current magnetic field Hac has the same value between the positive and negative polarities. The change of the resistance R substantially does not include the frequency component of the alternating current magnetic field Hac.

As shown in FIG. 7B, the characteristic of the resistance R shifts to the positive magnetic field H side when a positive signal magnetic field Hsig is applied. The resistance R becomes large for the alternating current magnetic field Hac on the positive side. The resistance R becomes small for the alternating current magnetic field Hac on the negative side.

As shown in FIG. 7C, the characteristic of the resistance R shifts to the negative magnetic field H side when a negative signal magnetic field Hsig is applied. The resistance R becomes small for the alternating current magnetic field Hac on the positive side. The resistance R becomes large for the alternating current magnetic field Hac on the negative side.

Change in the resistance R is different for the positive and negative of the alternating current magnetic field Hac when a signal magnetic field Hsig with non-zero magnitude is applied. An output voltage that has an alternating current frequency component corresponding to the signal magnetic field Hsig is generated.

The characteristics described above are obtained in the case where the signal magnetic field Hsig does not temporally change. The case where the signal magnetic field Hsig temporally changes is as follows. The frequency of the signal magnetic field Hsig is taken as a signal frequency fsig. The frequency of the alternating current magnetic field Hac is taken as fac. In such a case, an output that corresponds to the signal magnetic field Hsig is generated at frequencies of fac±fsig.

In the case where the signal magnetic field Hsig temporally changes, the signal frequency fsig is, for example, not more than 1 kHz. On the other hand, the alternating current frequency fac is sufficiently greater than the signal frequency fsig. For example, the alternating current frequency fac is not less than 10 times the signal frequency fsig.

For example, the signal magnetic field Hsig can be detected with high accuracy by extracting an output voltage having the same period (frequency) component (alternating current frequency component) as the period (the frequency) of the alternating current magnetic field Hac. In the magnetic sensor 110 according to the embodiment, the external magnetic field Hex (the signal magnetic field Hsig) can be detected with high sensitivity. According to the embodiment, the external magnetic field Hex (the signal magnetic field Hsig) and the alternating current magnetic field Hac due to the first current I1 can be efficiently applied to the first magnetic element 51. High sensitivity is obtained.

FIGS. 8 to 10B are schematic views illustrating a magnetic sensor according to the first embodiment.

Figure 8:
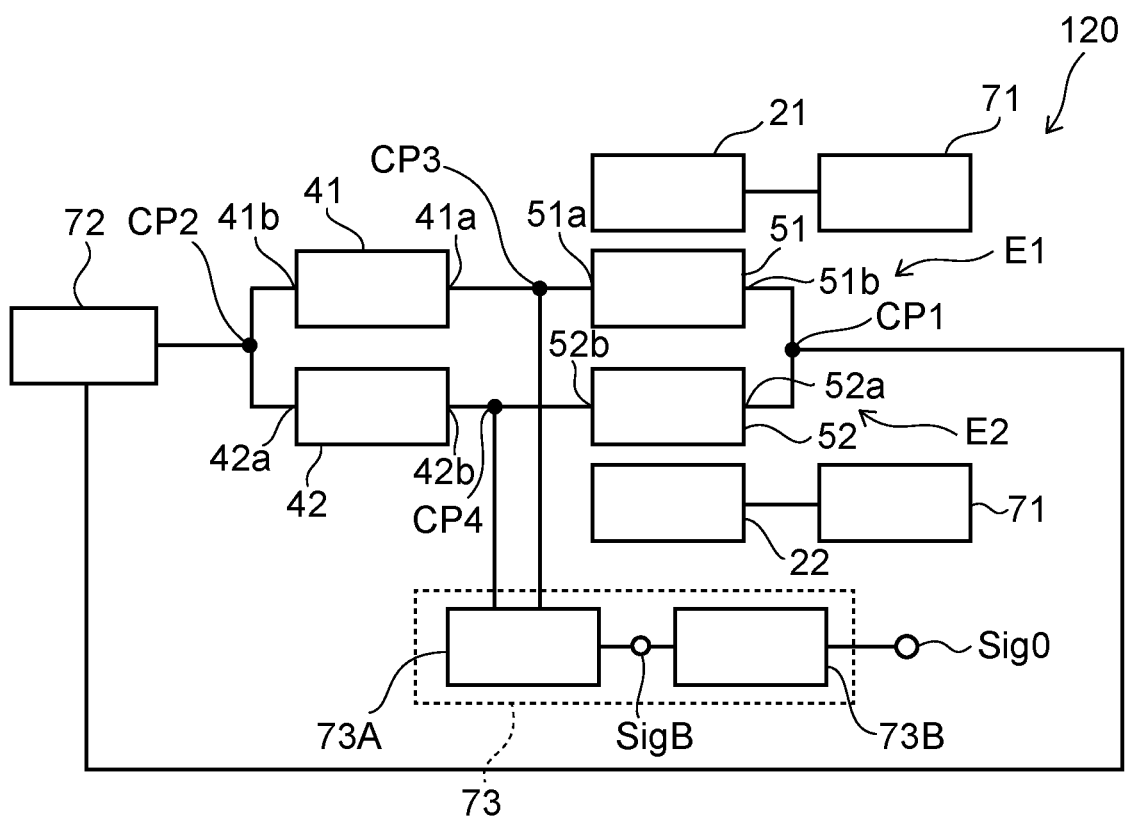
FIG. 8 is a schematic view illustrating a magnetic sensor according to the first embodiment.

As shown in FIG. 8, the magnetic sensor 120 according to the embodiment includes the first element part E1, a second element part E2, a first resistance element 41, a second resistance element 42, the first circuit 71, and the second circuit 72. The first element part E1 may have the configuration described above.

Figure 9:
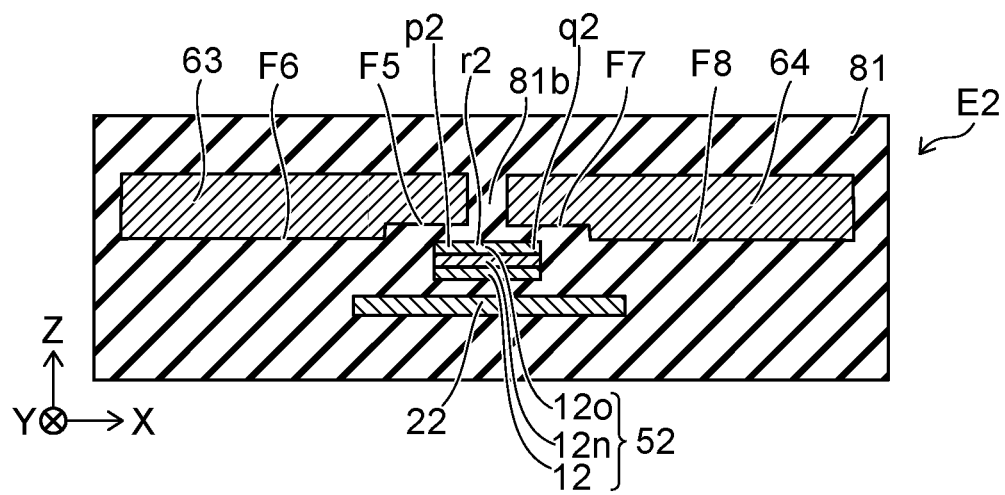
FIG. 9 is a schematic view illustrating the magnetic sensor according to the first embodiment.

As shown in FIGS. 8 and 9, the second element part E2 includes a second magnetic element 52 and a second conductive member 22.

Figure 10A:
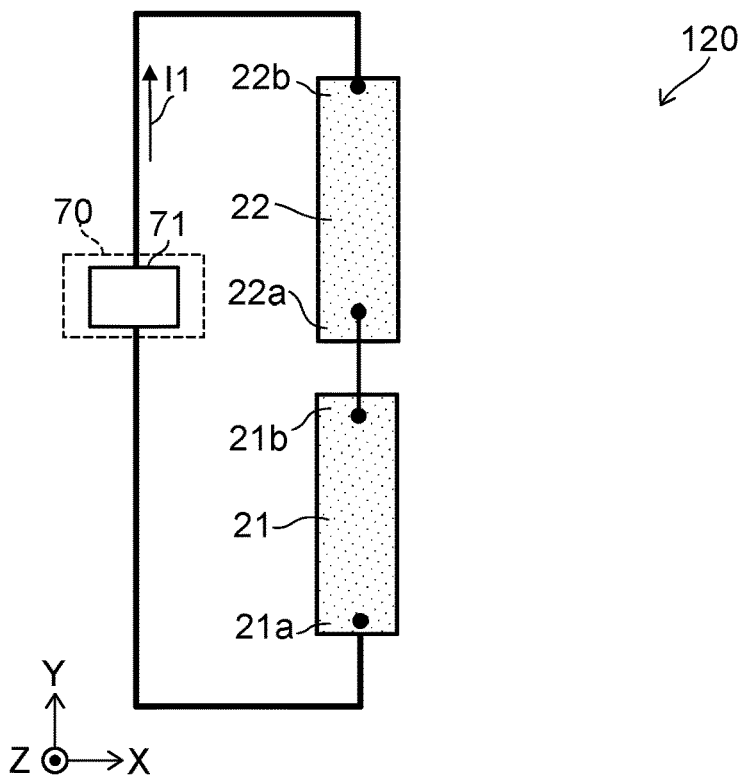
FIGS. 10A and 10B are schematic views illustrating the magnetic sensor according to the first embodiment.

As shown in FIG. 10A, the first conductive member 21 includes the first conductive portion 21a and the first other-conductive portion 21b. The second conductive member 22 includes a second conductive portion 22a and a second other-conductive portion 22b. The first other-conductive portion 21b is electrically connected to the second conductive portion 22a. The first circuit 71 is electrically connected to the first conductive portion 21a and the second other-conductive portion 22b. The first circuit 71 is configured to supply the first current I1 including the alternating current component between the first conductive portion 21a and the second other-conductive portion 22b.

Figure 10B:
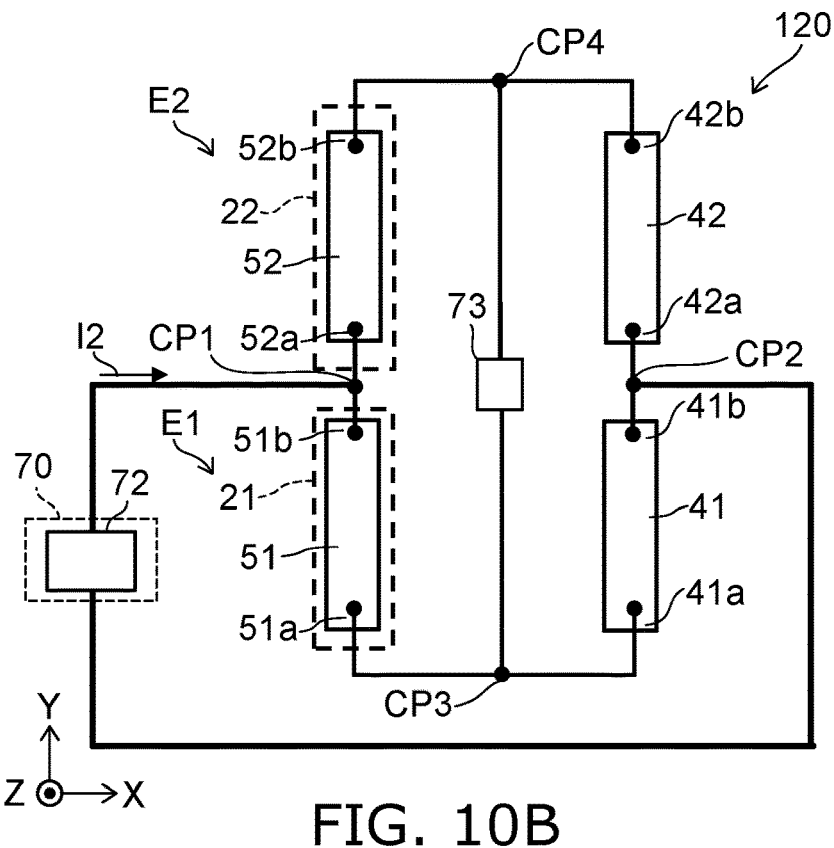

As shown in FIG. 10B, the first magnetic element 51 includes the first element portion 51a and the first other-element portion 51b. The second magnetic element 52 includes a second element portion 52a and a second other-element portion 52b. The first other-element portion 51b is electrically connected to the second element portion 52a. The first resistance element 41 includes a first resistance element portion 41a and a first other-resistance element portion 41b. The second resistance element 42 includes a second resistance element portion 42a and a second other-resistance element portion 42b. The first other-resistance element portion 41b is electrically connected to the second resistance element portion 42a. The first resistance element portion 41a is electrically connected to the first element portion 51a. The second other-resistance element portion 42b is electrically connected to the second other-element portion 52b. A bridge is formed of the first magnetic element 51, the second magnetic element 52, the first resistance element 41, and the second resistance element 42.

As shown in FIG. 10B, the second circuit 72 is electrically connected to a first connection point CP1 between the first other-element portion 51b and the second element portion 52a and a second connection point CP2 between the first other-resistance element portion 41b and the second resistance element portion 42a. The second circuit 72 is configured to supply the second current I2 between the first connection point CP1 and the second connection point CP2.

The orientation from the first conductive portion 21a toward the first other-conductive portion 21b is the same as the orientation from the first element portion 51a toward the first other-element portion 51b. The orientation from the second conductive portion 22a toward the second other-conductive portion 22b is the same as the orientation from the second element portion 52a toward the second other-element portion 52b.

As shown in FIG. 10B, the first magnetic element 51 overlaps the first conductive member 21 in the Z-axis direction. The second magnetic element 52 overlaps the second conductive member 22 in the Z-axis direction.

For example, the magnetic field (the alternating current magnetic field) due to the first current I1 flowing in the first conductive member 21 is applied to the first magnetic element 51. The magnetic field (the alternating current magnetic field) due to the first current I1 flowing in the second conductive member 22 is applied to the second magnetic element 52.

At one time, the first current I1 flows from the second other-conductive portion 22b toward the second conductive portion 22a and flows from the first other-conductive portion 21b toward the first conductive portion 21a. On the other hand, the second current I2 flows from the second element portion 52a toward the second other-element portion 52b and flows from the first other-element portion 51b toward the first element portion 51a. The orientation of the second current I2 flowing in the first magnetic element 51 is opposite to the orientation of the second current I2 flowing in the second magnetic element 52. On the other hand, the orientation (the polarity or the phase) of the first current I1 flowing in the first conductive member 21 is the same as the orientation (the polarity or the phase) of the first current I1 flowing in the second conductive member 22.

Due to such a configuration, the phase of the change of the electrical resistance of the first magnetic element 51 is opposite to the phase of the change of the electrical resistance of the second magnetic element 52. Unnecessary signal components can be efficiently removed by such a configuration in which the first magnetic element 51 and the second magnetic element 52 have a bridge connection. Higher sensitivity is easily obtained.

As shown in FIG. 10B, the magnetic sensor 120 may further include a third circuit 73. The third circuit 73 may be included in the circuit part 70. The third circuit 73 is electrically connected to a third connection point CP3 between the first resistance element portion 41a and the first element portion 51a and a fourth connection point CP4 between the second other-resistance element portion 42b and the second other-element portion 52b. The third circuit 73 is configured to detect the change of the potential between the third connection point CP3 and the fourth connection point CP4. The potential difference of the two midpoints of the bridge connection can be detected by the third circuit 73. Higher sensitivity is easily obtained.

In one example as shown in FIG. 8, the third circuit 73 includes a differential circuit portion 73A and a filter 73B. The differential circuit portion 73A is electrically connected to the third connection point CP3 and the fourth connection point CP4. The differential circuit portion 73A outputs a signal SigB corresponding to the difference between the potential of the third connection point CP3 and the potential of the fourth connection point CP4. The signal SigB is supplied to the filter 73B. The filter 73B can output a signal that corresponds to a frequency component of the signal SigB (e.g., the frequency of the alternating current component of the first current I1) as a signal Sig0.

In the example as shown in FIG. 9, for example, the second element part E2 includes a third magnetic member 63 and a fourth magnetic member 64 in addition to the second magnetic element 52 and the second conductive member 22. The fourth magnetic member 64 is separated from the third magnetic member 63 along the second direction (e.g., the X-axis direction).

The second magnetic element 52 includes a second magnetic layer 12, a second counter magnetic layer 12o, and a second nonmagnetic layer 12n provided between the second magnetic layer 12 and the second counter magnetic layer 12o. The direction from the second magnetic layer 12 toward the second counter magnetic layer 12o is along the first direction (the Z-axis direction). The second magnetic element 52 includes a second element region p2, a second other-element region q2, and a second intermediate element region r2. The second element region p2 is between a portion of the second conductive member 22 and a portion of the third magnetic member 63 in the first direction. The second other-element region q2 is between the fourth magnetic member 64 and another portion of the second conductive member 22 in the first direction. The second intermediate element region r2 is between the second element region p2 and the second other-element region q2 in the second direction (e.g., the X-axis direction). The second intermediate element region r2 overlaps a region 81b between the third magnetic member 63 and the fourth magnetic member 64 in the first direction (the Z-axis direction).

For example, the third magnetic member 63 includes a fifth partial surface F5 and a sixth partial surface F6. The fifth partial surface F5 faces the second element region p2 in the first direction (the Z-axis direction). The position in the second direction (the X-axis direction) of the fifth partial surface F5 is between the position in the second direction of the sixth partial surface F6 and the position in the second direction of the fourth magnetic member 64. The position in the first direction (the Z-axis direction) of the sixth partial surface F6 is between the position in the first direction of the second conductive member 22 and the position in the first direction of the fifth partial surface F5. Due to such a third magnetic member 63, for example, the magnetic field to be detected and the current magnetic field due to the second conductive member 22 are applied with high efficiency to the second magnetic element 52.

As shown in FIG. 9, for example, the fourth magnetic member 64 includes a seventh partial surface F7 and an eighth partial surface F8. The seventh partial surface F7 faces the second other-element region q2 in the first direction. The position in the second direction of the seventh partial surface F7 is between the position in the second direction of the third magnetic member 63 and the position in the second direction of the eighth partial surface F8. The position in the first direction of the eighth partial surface F8 is between the position in the first direction of the second conductive member 22 and the position in the first direction of the seventh partial surface F7. Due to such a fourth magnetic member 64, for example, the magnetic field to be detected and the current magnetic field due to the second conductive member 22 are applied with high efficiency to the second magnetic element 52.

FIGS. 11 to 13B are schematic views illustrating a magnetic sensor according to the first embodiment.

Figure 11:
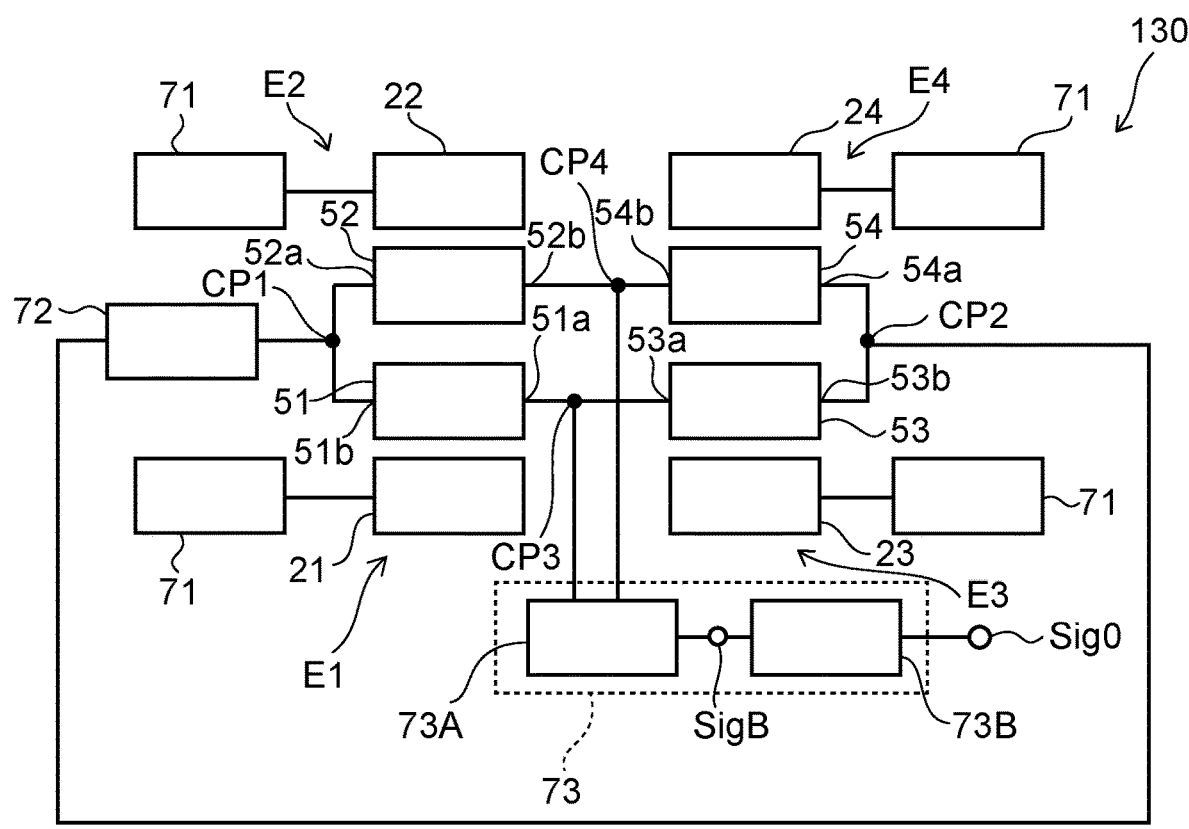
FIG. 11 is a schematic view illustrating a magnetic sensor according to the first embodiment.

As shown in FIG. 11, the magnetic sensor 130 according to the embodiment includes the first element part E1, the second element part E2, a third element part E3, a fourth element part E4, the first circuit 71, and the second circuit 72. The first element part E1 and the second element part E2 may have the configurations described above. For example, as described above, the first element part E1 includes the first magnetic element 51 and the first conductive member 21. The second element part E2 includes the second magnetic element 52 and the second conductive member 22.

Figure 12A:
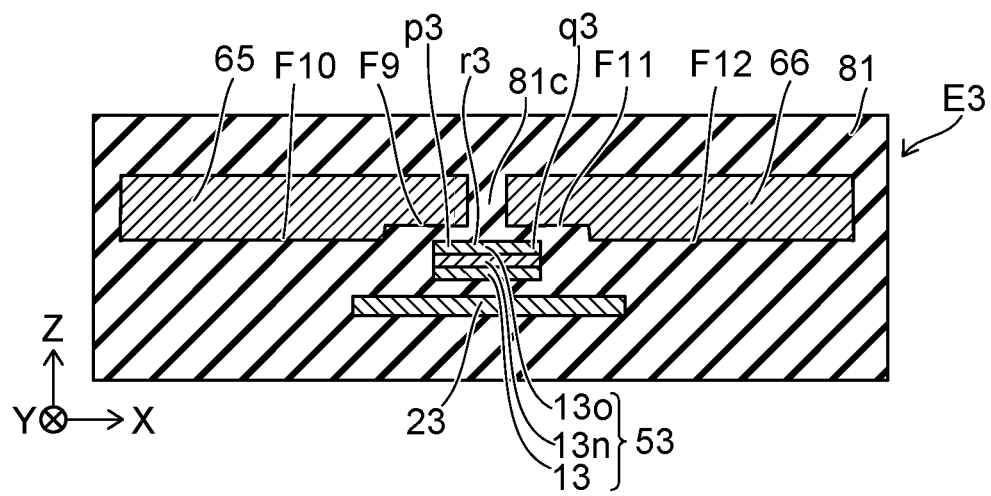
FIGS. 12A and 12B are schematic views illustrating the magnetic sensor according to the first embodiment.
Figure 12B:
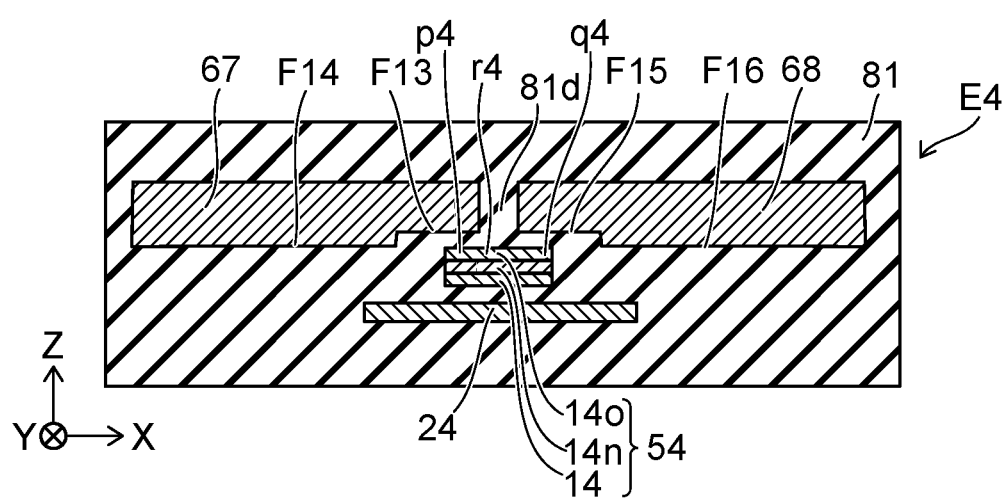

As shown in FIGS. 11 and 12A, the third element part E3 includes a third magnetic element 53 and a third conductive member 23. As shown in FIGS. 11 and 12B, the fourth element part E4 includes a fourth magnetic element 54 and a fourth conductive member 24.

Figure 13A:
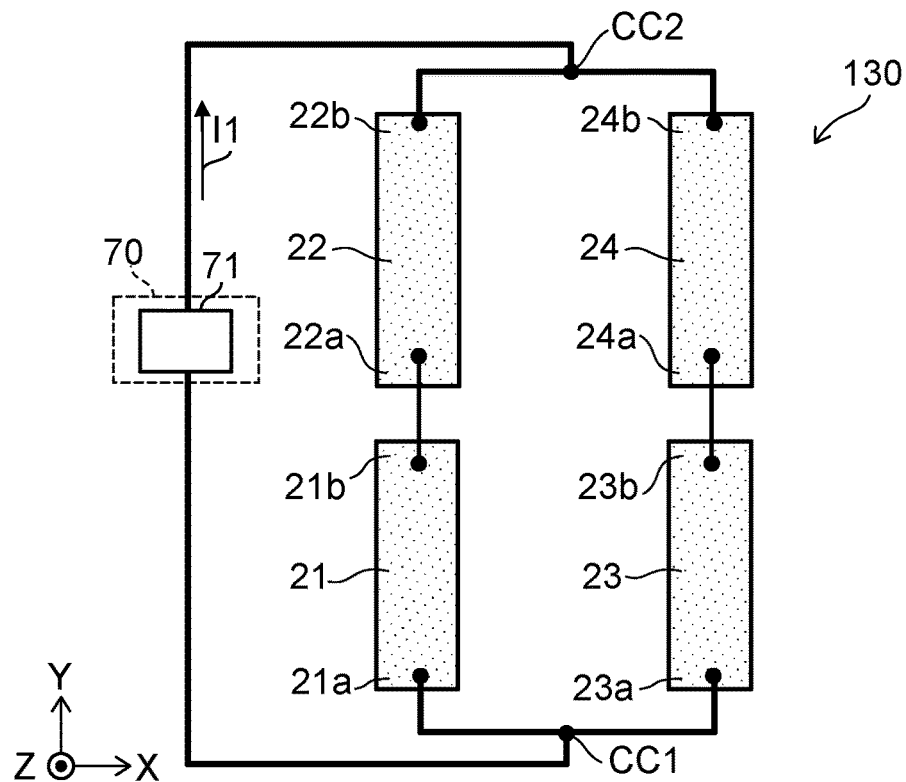
FIGS. 13A and 13B are schematic views illustrating the magnetic sensor according to the first embodiment.

As shown in FIG. 13A, the first conductive member 21 includes the first conductive portion 21a and the first other-conductive portion 21b. The second conductive member 22 includes the second conductive portion 22a and the second other-conductive portion 22b. The third conductive member 23 includes a third conductive portion 23a and a third other-conductive portion 23b. The fourth conductive member 24 includes a fourth conductive portion 24a and a fourth other-conductive portion 24b. The first conductive portion 21a is electrically connected to the third conductive portion 23a. The second other-conductive portion 22b is electrically connected to the fourth other-conductive portion 24b. The first other-conductive portion 21b is electrically connected to the second conductive portion 22a. The third other-conductive portion 23b is electrically connected to the fourth conductive portion 24a.

The first circuit 71 is electrically connected to a first conductive connection point CC1 between the first conductive portion 21a and the third conductive portion 23a and to a second conductive connection point CC2 between the second other-conductive portion 22b and the fourth other-conductive portion 24b. The first circuit 71 is configured to supply the first current I1 including the alternating current component between the first conductive connection point CC1 and the second conductive connection point CC2.

Figure 13B:
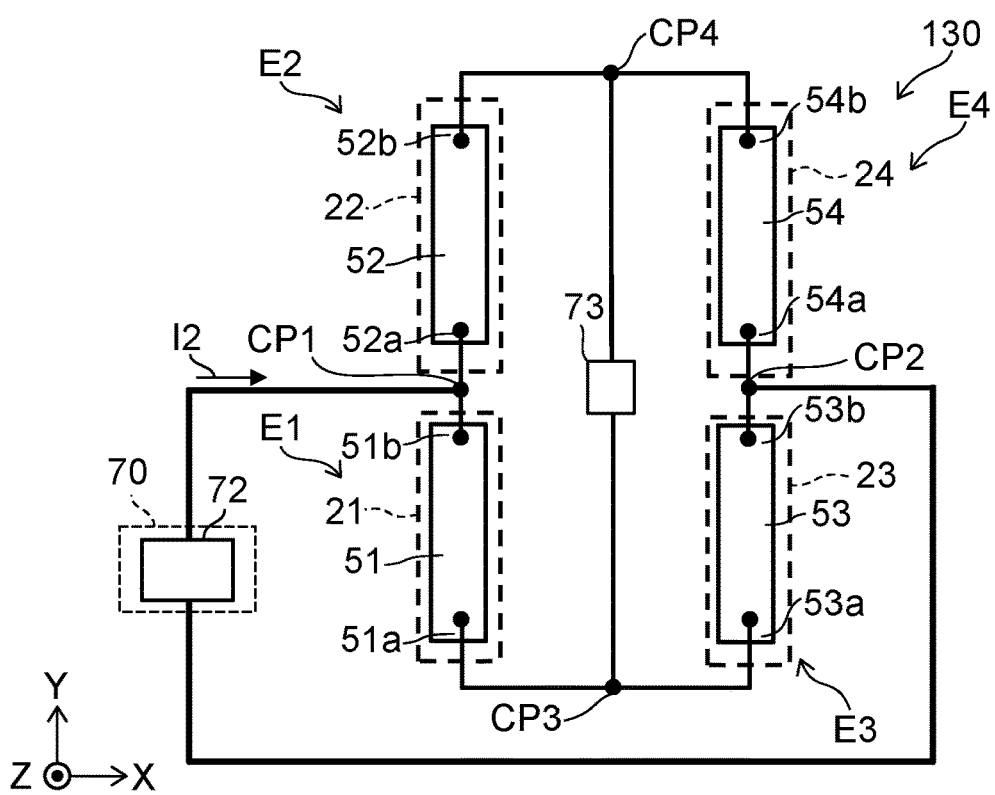

As shown in FIG. 13B, the first magnetic element 51 includes the first element portion 51a and the first other-element portion 51b. The second magnetic element 52 includes the second element portion 52a and the second other-element portion 52b. The third magnetic element 53 includes a third element portion 53a and a third other-element portion 53b. The fourth magnetic element 54 includes a fourth element portion 54a and a fourth other-element portion 54b. The first element portion 51a is electrically connected to the third element portion 53a. The second other-element portion 52b is electrically connected to the fourth other-element portion 54b. The first other-element portion 51b is electrically connected to the second element portion 52a. The third other-element portion 53b is electrically connected to the fourth element portion 54a.

The second circuit 72 is electrically connected to the first connection point CP1 between the first other-element portion 51b and the second element portion 52a and to the second connection point CP2 between the third other-element portion 53b and the fourth element portion 54a. The second circuit 72 is configured to supply the second current I2 between the first connection point CP1 and the second connection point CP2.

For example, unnecessary signal components are effectively suppressed by the four magnetic elements having a bridge connection. Higher sensitivity is obtained.

For example, the orientation from the first conductive portion 21a toward the first other-conductive portion 21b is the same as the orientation from the first element portion 51a toward the first other-element portion 51b. The orientation from the second conductive portion 22a toward the second other-conductive portion 22b is the same as the orientation from the second element portion 52a toward the second other-element portion 52b. The orientation from the third conductive portion 23a toward the third other-conductive portion 23b is the same as the orientation from the third element portion 53a toward the third other-element portion 53b. The orientation from the fourth conductive portion 24a toward the fourth other-conductive portion 24b is the same as the orientation from the fourth element portion 54a toward the fourth other-element portion 54b.

For example, the magnetic field due to the first current I1 flowing in the first conductive member 21 is applied to the first magnetic element 51. The magnetic field due to the first current I1 flowing in the second conductive member 22 is applied to the second magnetic element 52. The magnetic field due to the first current I1 flowing in the third conductive member 23 is applied to the third magnetic element 53. The magnetic field due to the first current I1 flowing in the fourth conductive member 24 is applied to the fourth magnetic element 54.

For example, the orientation of the second current I2 flowing in the first magnetic element 51 is opposite to the orientation of the second current I2 flowing in the second magnetic element 52. The orientation (the polarity or the phase) of the first current I1 flowing in the first conductive member 21 is the same as the orientation (the polarity or the phase) of the first current I1 flowing in the second conductive member 22. The orientation of the second current I2 flowing in the third magnetic element 53 is opposite to the orientation of the second current I2 flowing in the fourth magnetic element 54. The orientation (the polarity or the phase) of the first current I1 flowing in the third conductive member 23 is the same as the orientation (the polarity or the phase) of the first current I1 flowing in the fourth conductive member 24. Unnecessary signal components can be easily removed by using a bridge connection for magnetic elements to which current magnetic fields having opposite phases when referenced to the orientation of the second current I2 flowing in the magnetic element are applied. High sensitivity is easily obtained.

As shown in FIG. 13B, the magnetic sensor 130 may include the third circuit 73. The third circuit 73 is electrically connected to the third connection point CP3 between the first element portion 51a and the third element portion 53a and the fourth connection point CP4 between the second other-element portion 52b and the fourth other-element portion 54b. The third circuit 73 is configured to detect the change of the potential between the third connection point CP3 and the fourth connection point CP4.

As shown in FIG. 12A, the third element part E3 may include a fifth magnetic member 65 and a sixth magnetic member 66. The sixth magnetic member 66 is separated from the fifth magnetic member 65 along the second direction (e.g., the X-axis direction). The third magnetic element 53 includes a third magnetic layer 13, a third counter magnetic layer 13o, and a third nonmagnetic layer 13n provided between the third magnetic layer 13 and the third counter magnetic layer 13o. The direction from the third magnetic layer 13 toward the third counter magnetic layer 13o is along the first direction (the Z-axis direction).

The third magnetic element 53 includes a third element region p3, a third other-element region q3, and a third intermediate element region r3. The third element region p3 is between a portion of the third conductive member 23 and a portion of the fifth magnetic member 65 in the first direction (the Z-axis direction). The third other-element region q3 is between the sixth magnetic member 66 and another portion of the third conductive member 23 in the first direction. The third intermediate element region r3 is between the third element region p3 and the third other-element region q3 in the second direction (the X-axis direction). The third intermediate element region r3 overlaps a region 81c between the fifth magnetic member 65 and the sixth magnetic member 66 in the first direction (the Z-axis direction).

As shown in FIG. 12A, for example, the fifth magnetic member 65 includes a ninth partial surface F9 and a tenth partial surface F10. The ninth partial surface F9 faces the third element region p3 in the first direction (the Z-axis direction). The position in the second direction (the X-axis direction) of the ninth partial surface F9 is between the position in the second direction of the tenth partial surface F10 and the position in the second direction of the sixth magnetic member 66. The position in the first direction (the Z-axis direction) of the tenth partial surface F10 is between the position in the first direction of the third conductive member 23 and the position in the first direction of the ninth partial surface F9. For example, due to such a fifth magnetic member 65, the magnetic field to be detected and the current magnetic field due to the third conductive member 23 are applied with high efficiency to the third magnetic element 53.

As shown in FIG. 12A, for example, the sixth magnetic member 66 includes an eleventh partial surface F11 and a twelfth partial surface F12. The eleventh partial surface F11 faces the third other-element region q3 in the first direction. The position in the second direction of the eleventh partial surface F11 is between the position in the second direction of the fifth magnetic member 65 and the position in the second direction of the twelfth partial surface F12. The position in the first direction of the twelfth partial surface F12 is between the position in the first direction of the third conductive member 23 and the position in the first direction of the eleventh partial surface F11. For example, due to such a sixth magnetic member 66, the magnetic field to be detected and the current magnetic field due to the third conductive member 23 are applied with high efficiency to the third magnetic element 53.

As shown in FIG. 12B, the fourth element part E4 may further include a seventh magnetic member 67 and an eighth magnetic member 68. The eighth magnetic member 68 is separated from the seventh magnetic member 67 along the second direction (e.g., the X-axis direction). The fourth magnetic element 54 includes a fourth magnetic layer 14, a fourth counter magnetic layer 14o, and a fourth nonmagnetic layer 14n provided between the fourth magnetic layer 14 and the fourth counter magnetic layer 14o. The direction from the fourth magnetic layer 14 toward the fourth counter magnetic layer 14o is along the first direction (the Z-axis direction).

The fourth magnetic element 54 includes, for example, a fourth element region p4, a fourth other-element region q4, and a fourth intermediate element region r4. The fourth element region p4 is between a portion of the fourth conductive member 24 and a portion of the seventh magnetic member 67 in the first direction (the Z-axis direction). The fourth other-element region q4 is between the eighth magnetic member 68 and another portion of the fourth conductive member 24 in the first direction. The fourth intermediate element region r4 is between the fourth element region p4 and the fourth other-element region q4 in the second direction (the X-axis direction). The fourth intermediate element region r4 overlaps a region 81d between the seventh magnetic member 67 and the eighth magnetic member 68 in the first direction (the Z-axis direction).

As shown in FIG. 12B, the seventh magnetic member 67 includes a thirteenth partial surface F13 and a fourteenth partial surface F14. The thirteenth partial surface F13 faces the fourth element region p4 in the first direction (the Z-axis direction). The position in the second direction (e.g., the X-axis direction) of the thirteenth partial surface F13 is between the position in the second direction of the fourteenth partial surface F14 and the position in the second direction of the eighth magnetic member 68. The position in the first direction (the Z-axis direction) of the fourteenth partial surface F14 is between the position in the first direction of the fourth conductive member 24 and the position in the first direction of the thirteenth partial surface F13. For example, due to such a seventh magnetic member 67, the magnetic field to be detected and the current magnetic field due to the fourth conductive member 24 are applied with high efficiency to the fourth magnetic element 54.

As shown in FIG. 12B, for example, the eighth magnetic member 68 includes a fifteenth partial surface F15 and a sixteenth partial surface F16. The fifteenth partial surface F15 faces the fourth other-element region q4 in the first direction. The position in the second direction of the fifteenth partial surface F15 is between the position in the second direction of the seventh magnetic member 67 and the position in the second direction of the sixteenth partial surface F16. The position in the first direction of the sixteenth partial surface F16 is between the position in the first direction of the fourth conductive member 24 and the position in the first direction of the fifteenth partial surface F15. For example, due to such an eighth magnetic member 68, the magnetic field to be detected and the current magnetic field due to the fourth conductive member 24 are applied with high efficiency to the fourth magnetic element 54.

A configuration (includes materials) similar to that of the first magnetic element 51 is applicable to the second to fourth magnetic elements 52 to 54. Configurations (including materials) similar to those of the first and second magnetic members 61 and 62 are applicable to the third to eighth magnetic members 63 to 68.

Second Embodiment

A second embodiment relates to an inspection device. As described below, the inspection device may include a diagnostic device.

Figure 14:
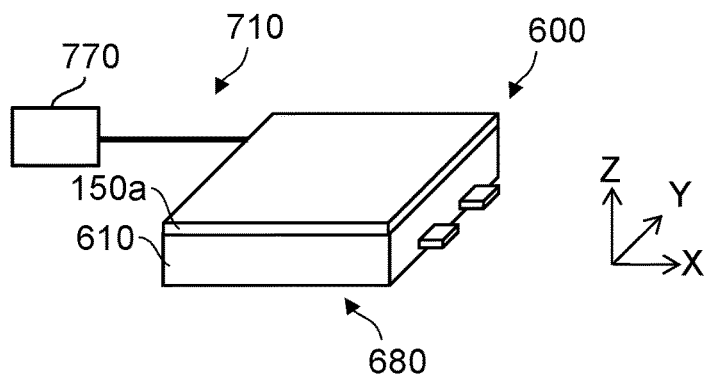
FIG. 14 is a schematic perspective view showing an inspection device according to a second embodiment.

FIG. 14 is a schematic perspective view showing the inspection device according to the second embodiment.

As shown in FIG. 14, the inspection device 710 according to the second embodiment includes a magnetic sensor 150a and a processor 770. The magnetic sensor 150a may be the magnetic sensor according to the first embodiment or a modification of the magnetic sensor. The processor 770 processes an output signal obtained from the magnetic sensor 150a. The processor 770 may perform a comparison between a reference value and the signal obtained from the magnetic sensor 150a, etc. The processor 770 is configured to output an inspection result based on the processing result.

For example, an inspection object 680 is inspected by the inspection device 710. The inspection object 680 is, for example, an electronic device (including a semiconductor circuit, etc.). The inspection object 680 may be, for example, a battery 610, etc.

For example, the magnetic sensor 150a according to the embodiment may be used with the battery 610. For example, a battery system 600 includes the battery 610 and the magnetic sensor 150a. The magnetic sensor 150a can detect a magnetic field generated by a current flowing in the battery 610.

Figure 15:
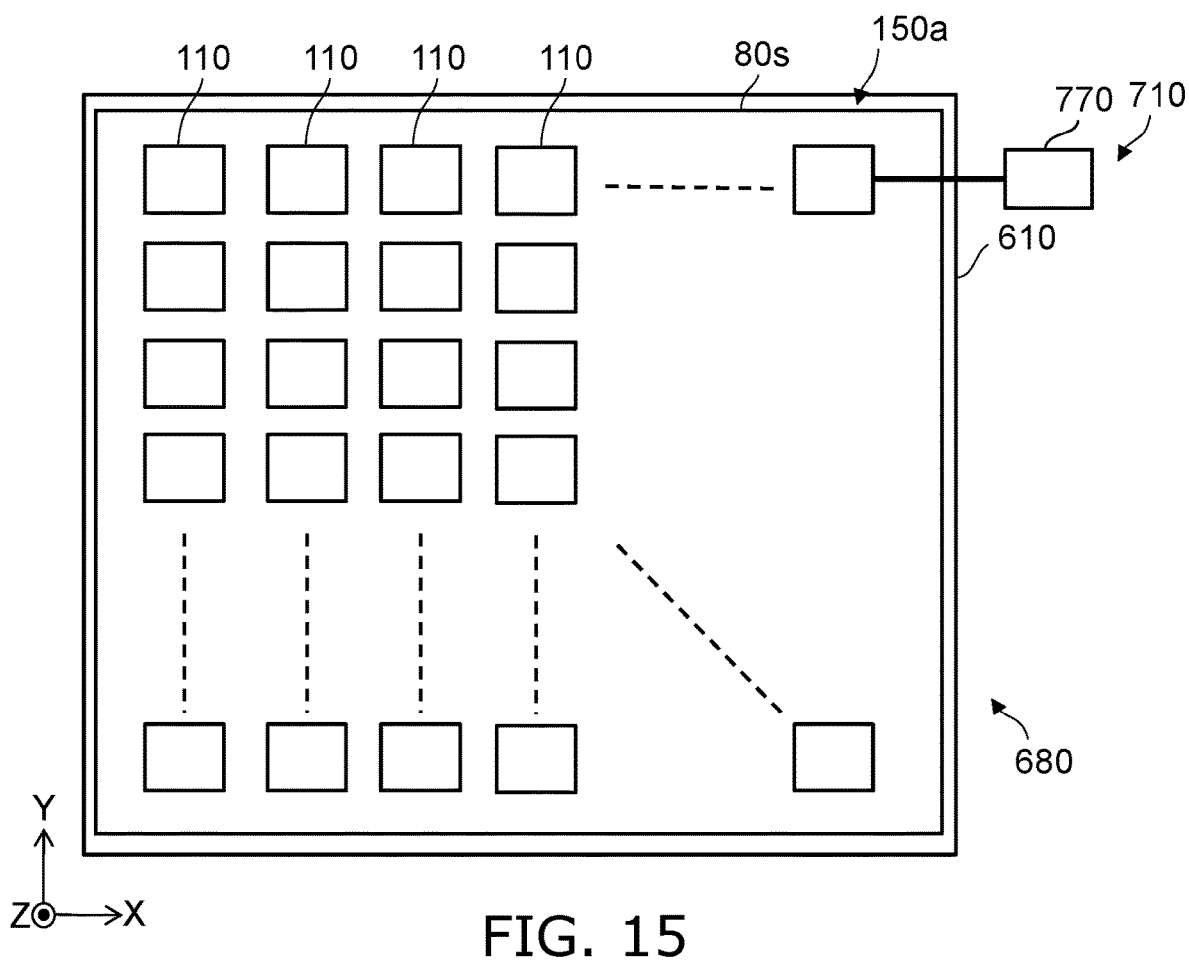
FIG. 15 is a schematic plan view showing the inspection device according to the second embodiment.

FIG. 15 is a schematic plan view showing the inspection device according to the second embodiment.

As shown in FIG. 15, the magnetic sensor 150a includes, for example, multiple magnetic sensors according to the embodiment. In the example, the magnetic sensor 150a includes multiple magnetic sensors (the magnetic sensors 110, 120, or 130, etc.). For example, the multiple magnetic sensors are arranged along two directions (e.g., the X-axis direction and the Y-axis direction). For example, the multiple magnetic sensors 110 are provided on a substrate.

The magnetic sensor 150a can detect a magnetic field generated by a current flowing in the inspection object 680 (which may be, for example, the battery 610). For example, an abnormal current flows in the battery 610 when the battery 610 is in an abnormal state. The state of the battery 610 can be known by detecting the abnormal current by the magnetic sensor 150a. For example, the entire battery 610 can be inspected in a short period of time by moving the sensor array to two directions with keeping the magnetic sensor array 150a proximate to the battery 610. The magnetic sensor 150a may be used to inspect the battery 610 in the manufacturing process of the battery 610.

Figure 16:
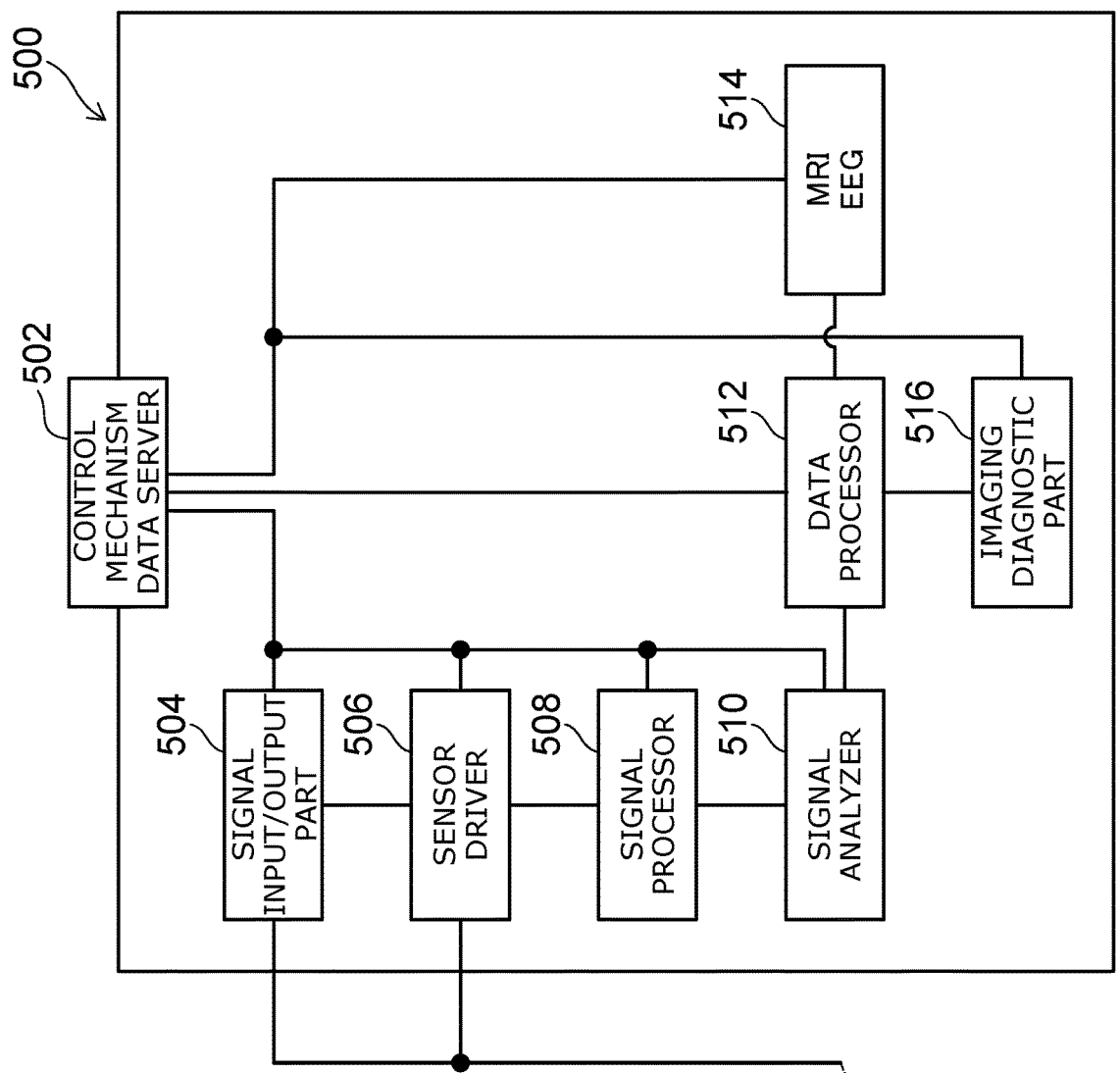
FIG. 16 is a schematic view showing the magnetic sensor and the inspection device according to the embodiment.
Figure 16:
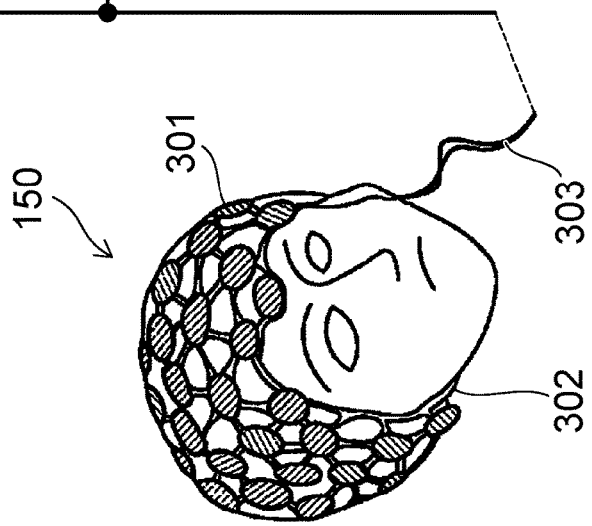

For example, the magnetic sensor according to the embodiment is applicable to the inspection device 710 such as a diagnostic device, etc. FIG. 16 is a schematic view showing the magnetic sensor and the inspection device according to the embodiment.

As shown in FIG. 16, the diagnostic device 500 is an example of the inspection device 710 and includes the magnetic sensor 150. The magnetic sensor 150 includes the magnetic sensor described in reference to the first embodiment and modifications of the magnetic sensor.

In the diagnostic device 500, the magnetic sensor 150 is, for example, a magnetoencephalography device. The magnetoencephalography device detects a magnetic field generated by cranial nerves. When the magnetic sensor 150 is included in a magnetoencephalography device, the size of the magnetic element included in the magnetic sensor 150 is, for example, not less than 1 mm but less than 10 mm. The size is, for example, the length including the MFC.

As shown in FIG. 16, the magnetic sensor 150 (the magnetoencephalography device) is mounted to, for example, the head of a human body. The magnetic sensor 150 (the magnetoencephalography device) includes a sensor part 301. The magnetic sensor 150 (the magnetoencephalography device) may include multiple sensor parts 301. The number of the multiple sensor parts 301 is, for example, about 100 (e.g., not less than 50 and not more than 150). The multiple sensor parts 301 are provided on a flexible base body 302.

The magnetic sensor 150 may include, for example, a circuit for differential detection, etc. The magnetic sensor 150 may include a sensor other than a magnetic sensor (e.g., a potential terminal, an acceleration sensor, etc.).

The size of the magnetic sensor 150 is small compared to the size of a conventional SQUID magnetic sensor. Therefore, the mounting of the multiple sensor parts 301 is easy. The mounting of the multiple sensor parts 301 and the other circuits is easy. The mounting of both multiple sensor parts 301 and the other sensors is easy.

The base body 302 may include, for example, an elastic body such as a silicone resin, etc. For example, the multiple sensor parts 301 are linked to each other and provided in the base body 302. For example, the base body 302 can be closely adhered to the head.

An input/output cord 303 of the sensor part 301 is connected to a sensor driver 506 and a signal input/output part 504 of the diagnostic device 500. Magnetic field measurement is performed in the sensor part 301 based on the electrical power from the sensor driver 506 and the control signal from the signal input/output part 504. The result is input to the signal input/output part 504. The signal that is obtained by the signal input/output part 504 is supplied to a signal processor 508. Signal processing such as, for example, the removal of noise, filtering, amplification, signal calculation, etc., are performed in the signal processor 508. The signal that is processed by the signal processor 508 is supplied to a signal analyzer 510. For example, the signal analyzer 510 extracts a designated signal for magnetoencephalography. For example, signal analysis to match the signal phases is performed in the signal analyzer 510.

The output of the signal analyzer 510 (the data for which the signal analysis is finished) is supplied to a data processor 512. Data analysis is performed in the data processor 512. It is possible to include image data such as, for example, MRI (Magnetic Resonance Imaging), etc., in the data analysis. It is possible to include, for example, scalp potential information such as an EEG (Electroencephalogram), etc., in the data analysis. For example, nerve firing point analysis, inverse analysis, or the like is performed by the data analysis.

For example, the result of the data analysis is supplied to an imaging diagnostic part 516. Imaging is performed by the imaging diagnostic part 516. The diagnosis is supported by the imaging.

For example, the series of operations described above is controlled by a control mechanism 502. For example, necessary data such as preliminary signal data, metadata partway through the data processing, etc., is stored in a data server. The data server and the control mechanism may be integrated.

The diagnostic device 500 according to the embodiment includes the magnetic sensor 150, and a processor that processes the output signal obtained from the magnetic sensor 150. The processor includes, for example, at least one of the signal processor 508 or the data processor 512. The processor includes, for example, a computer, etc.

In the magnetic sensor 150 shown in FIG. 16, the sensor part 301 is mounted to the head of a human body. The sensor part 301 may be mounted to the chest of the human body. Magnetocardiography is possible thereby. For example, the sensor part 301 may be mounted to the abdomen of a pregnant woman. Palmoscopy of the fetus can be performed thereby.

It is favorable for the magnetic sensor device including the participant to be mounted inside a shielded room. For example, the effects of geomagnetism or magnetic noise can be suppressed thereby.

For example, a mechanism may be provided to locally shield the sensor part 301 or the measurement section of the human body. For example, a shield mechanism may be provided in the sensor part 301. For example, the signal analysis or the data processing may be effectively shielded.

According to the embodiment, the base body 302 may be flexible or may be substantially not flexible. In the example shown in FIG. 16, the base body 302 is a continuous film that is patterned into a hat-like configuration. The base body 302 may have a net configuration. For example, it fits well to the body. For example, the adhesion of the base body 302 to the human body is improved. The base body 302 may have a hard helmet-like configuration.

Figure 17:
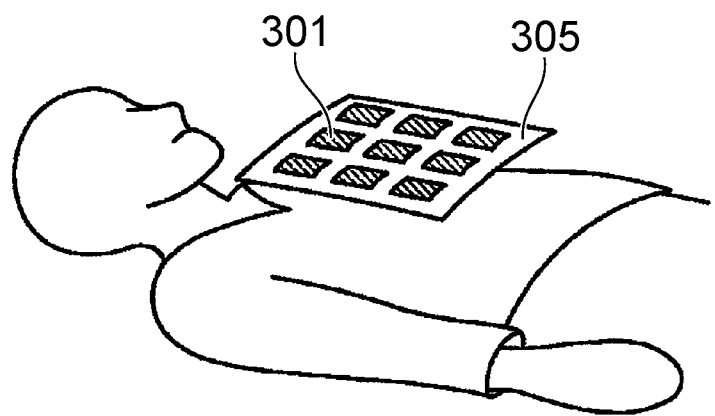
FIG. 17 is a schematic view showing the inspection device according to the embodiment.

FIG. 17 is a schematic view showing the inspection device according to the embodiment.

FIG. 17 is an example of a magnetic detection instrument. In the example shown in FIG. 17, the sensor part 301 is provided on a hard base body 305 having a flat plate shape.

The input and output of the signal obtained from the sensor part 301 in the example shown in FIG. 17 are similar to the input and output described with reference to FIG. 16. The signal processing of the signal obtained from the sensor part 301 in the example shown in FIG. 17 is similar to the signal processing described with reference to FIG. 16.

There is a reference example in which a SQUID (Superconducting Quantum Interference Device) magnetic sensor is used as a device to measure a faint magnetic field such as a magnetic field generated from a living body, etc. Because superconductivity is used in the reference example, the device is large; and the power consumption is large. The load of the measurement object (the patient) is large.

According to the embodiment, the device can be small. The power consumption can be suppressed. The load on the measurement object (the patient) can be reduced. According to the embodiment, the SN ratio of the magnetic field detection can be improved. The sensitivity can be increased.

Embodiments may include the following configurations (e.g., technological proposals).

Configuration 1

A magnetic sensor, comprising:
a first element part including
a first magnetic element, the first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction, a first conductive member, a first magnetic member, and a second magnetic member, the second magnetic member being separated from the first magnetic member along a second direction crossing the first direction, the first magnetic element including a first element region, a first other-element region, and a first intermediate element region, the first element region being between a portion of the first conductive member and a portion of the first magnetic member in the first direction, the first other-element region being between the second magnetic member and an other portion of the first conductive member in the first direction, the first intermediate element region being between the first element region and the first other-element region in the second direction, the first intermediate element region overlapping a region between the first magnetic member and the second magnetic member in the first direction, the first magnetic member including a first partial surface and a second partial surface, the first partial surface facing the first element region in the first direction, a position in the second direction of the first partial surface being between a position in the second direction of the second partial surface and a position in the second direction of the second magnetic member, a position in the first direction of the second partial surface being between a position in the first direction of the first conductive member and a position in the first direction of the first partial surface.

Configuration 2

The magnetic sensor according to Configuration 1, wherein a portion of the first conductive member overlaps at least a portion of the second partial surface in the first direction.

Configuration 3

The magnetic sensor according to Configuration 1 or 2, wherein the second magnetic member includes a third partial surface and a fourth partial surface, the third partial surface faces the first other-element region in the first direction, a position in the second direction of the third partial surface is between a position in the second direction of the first magnetic member and a position in the second direction of the fourth partial surface, and a position in the first direction of the fourth partial surface is between the position in the first direction of the first conductive member and a position in the first direction of the third partial surface.

Configuration 4

The magnetic sensor according to any one of Configurations 1 to 3, wherein the first magnetic member includes a first partial side surface between the first partial surface and the second partial surface, and the first partial side surface is oblique to the first partial surface.

Configuration 5

The magnetic sensor according to Configuration 4, wherein an angle between the first partial side surface and the first partial surface is not less than 95 degrees and not more than 175 degrees.

Configuration 6

The magnetic sensor according to any one of Configurations 1 to 5, wherein a distance along the first direction between the position in the first direction of the first partial surface and the position in the first direction of the second partial surface is not less than 100 nm.

Configuration 7

The magnetic sensor according to any one of Configurations 1 to 6, wherein the first magnetic layer and the first counter magnetic layer include Fe and Co, and the first magnetic member and the second magnetic member include Fe, Co, and Ni.

Configuration 8

The magnetic sensor according to any one of Configurations 1 to 7, wherein the first element region includes a portion facing the first partial surface in the first direction, and a length along the second direction of the facing portion is not less than 0.1 times and not more than 0.9 times a length along the second direction of the first magnetic element.

Configuration 9

The magnetic sensor according to any one of Configurations 1 to 5, wherein the first magnetic element includes:
a third-direction length along a third direction crossing a plane including the first and second directions; and
a second-direction length along the second direction, and
the third-direction length is greater than the second-direction length.

Configuration 10

The magnetic sensor according to Configuration 9, further comprising:

a first circuit, the first conductive member including a first conductive portion and a first other-conductive portion, a direction from the first conductive portion toward the first other-conductive portion being along the third direction, the first circuit being electrically connected to the first conductive portion and the first other-conductive portion, and being configured to supply a first current including an alternating current component between the first conductive portion and the first other-conductive portion.

Configuration 11

The magnetic sensor according to Configuration 10, further comprising:

a second circuit, the first magnetic element including a first element portion and a first other-element portion, a direction from the first element portion toward the first other-element portion being along the third direction, the second circuit being electrically connected to the first element portion and the first other-element portion, and being configured to supply a second current between the first element portion and the first other-element portion.

Configuration 12

The magnetic sensor according to Configuration 9, further comprising:

a second element part;

a first resistance element;

a second resistance element;

a first circuit; and a second circuit, the second element part including a second magnetic element and a second conductive member, the first conductive member including a first conductive portion and a first other-conductive portion, the second conductive member including a second conductive portion and a second other-conductive portion, the first other-conductive portion being electrically connected to the second conductive portion, the first circuit being electrically connected to the first conductive portion and the second other-conductive portion, and being configured to supply a first current including an alternating current component between the first conductive portion and the second other-conductive portion, the first magnetic element including a first element portion and a first other-element portion, the second magnetic element including a second element portion and a second other-element portion, the first other-element portion being electrically connected to the second element portion, the first resistance element including a first resistance element portion and a first other-resistance element portion, the second resistance element including a second resistance element portion and a second other-resistance element portion, the first other-resistance element portion being electrically connected to the second resistance element portion, the first resistance element portion being electrically connected to the first element portion, the second other-resistance element portion being electrically connected to the second other-element portion, the second circuit being electrically connected to a first connection point and a second connection point, the first connection point being between the first other-element portion and the second element portion, the second connection point being between the first other-resistance element portion and the second resistance element portion, the second circuit being configured to supply a second current between the first connection point and the second connection point.

Configuration 13

The magnetic sensor according to Configuration 12, wherein an orientation from the first conductive portion toward the first other-conductive portion is the same as an orientation from the first element portion toward the first other-element portion, and an orientation from the second conductive portion toward the second other-conductive portion is the same as an orientation from the second element portion toward the second other-element portion.

Configuration 14

The magnetic sensor according to Configuration 12 or 13, further comprising:

a third circuit, the third circuit being electrically connected to a third connection point and a fourth connection point, the third connection point being between the first resistance element portion and the first element portion, the fourth connection point being between the second other-resistance element portion and the second other-element portion, the third circuit being configured to detect a change of a potential between the third connection point and the fourth connection point.

Configuration 15

The magnetic sensor according to Configuration 9, further comprising:

a second element part;

a third element part;

a fourth element part;

a first circuit; and a second circuit, the second element part including a second magnetic element and a second conductive member, the third element part including a third magnetic element and a third conductive member, the fourth element part including a fourth magnetic element and a fourth conductive member, the first conductive member including a first conductive portion and a first other-conductive portion, the second conductive member including a second conductive portion and a second other-conductive portion, the third conductive member including a third conductive portion and a third other-conductive portion, the fourth conductive member including a fourth conductive portion and a fourth other-conductive portion, the first conductive portion being electrically connected to the third conductive portion, the second other-conductive portion being electrically connected to the fourth other-conductive portion, the first other-conductive portion being electrically connected to the second conductive portion, the third other-conductive portion being electrically connected to the fourth conductive portion, the first circuit being electrically connected to a first conductive connection point and a second conductive connection point, the first conductive connection point being between the first conductive portion and the third conductive portion, the second conductive connection point being between the second other-conductive portion and the fourth other-conductive portion, the first circuit being configured to supply a first current including an alternating current component between the first conductive connection point and the second conductive connection point, the first magnetic element including a first element portion and a first other-element portion, the second magnetic element including a second element portion and a second other-element portion, the third magnetic element including a third element portion and a third other-element portion, the fourth magnetic element including a fourth element portion and a fourth other-element portion, the first element portion being electrically connected to the third element portion, the second other-element portion being electrically connected to the fourth other-element portion, the first other-element portion being electrically connected to the second element portion, the third other-element portion being electrically connected to the fourth element portion, the second circuit being electrically connected to a first connection point and a second connection point, the first connection point being between the first other-element portion and the second element portion, the second connection point being between the third other-element portion and the fourth element portion, the second circuit being configured to supply a second current between the first connection point and the second connection point.

Configuration 16

The magnetic sensor according to Configuration 15, wherein an orientation from the first conductive portion toward the first other-conductive portion is the same as an orientation from the first element portion toward the first other-element portion, an orientation from the second conductive portion toward the second other-conductive portion is the same as an orientation from the second element portion toward the second other-element portion, an orientation from the third conductive portion toward the third other-conductive portion is the same as an orientation from the third element portion toward the third other-element portion, an orientation from the fourth conductive portion toward the fourth other-conductive portion is the same as an orientation from the fourth element portion toward the fourth other-element portion.

Configuration 17

The magnetic sensor according to Configuration 15 or 16, wherein a magnetic field due to the first current flowing in the first conductive member is applied to the first magnetic element, a magnetic field due to the first current flowing in the second conductive member is applied to the second magnetic element, a magnetic field due to the first current flowing in the third conductive member is applied to the third magnetic element, and a magnetic field due to the first current flowing in the fourth conductive member is applied to the fourth magnetic element.

Configuration 18

The magnetic sensor according to any one of Configurations 15 to 17, further comprising:

a third circuit, the third circuit being electrically connected to a third connection point and a fourth connection point, the third connection point being between the first element portion and the third element portion, the fourth connection point being between the second other-element portion and the fourth other-element portion, the third circuit being configured to detect a change of a potential between the third connection point and the fourth connection point.

Configuration 19

The magnetic sensor according to any one of Configurations 15 to 18, wherein the second element part further includes a third magnetic member and a fourth magnetic member, the fourth magnetic member is separated from the third magnetic member along the second direction, the second magnetic element includes a second magnetic layer, a second counter magnetic layer, and a second nonmagnetic layer provided between the second magnetic layer and the second counter magnetic layer, a direction from the second magnetic layer toward the second counter magnetic layer is along the first direction, the second magnetic element includes a second element region, a second other-element region, and a second intermediate element region, the second element region is between a portion of the second conductive member and a portion of the third magnetic member in the first direction, the second other-element region is between the fourth magnetic member and an other portion of the second conductive member in the first direction, the second intermediate element region is between the second element region and the second other-element region in the second direction, the second intermediate element region overlaps a region between the third magnetic member and the fourth magnetic member in the first direction, the third magnetic member includes a fifth partial surface and a sixth partial surface, the fifth partial surface faces the second element region in the first direction, a position in the second direction of the fifth partial surface is between a position in the second direction of the sixth partial surface and a position in the second direction of the fourth magnetic member, a position in the first direction of the sixth partial surface is between a position in the first direction of the second conductive member and a position in the first direction of the fifth partial surface, the third element part further includes a fifth magnetic member and a sixth magnetic member, the sixth magnetic member is separated from the fifth magnetic member along the second direction, the third magnetic element includes a third magnetic layer, a third counter magnetic layer, and a third nonmagnetic layer provided between the third magnetic layer and the third counter magnetic layer, a direction from the third magnetic layer toward the third counter magnetic layer is along the first direction, the third magnetic element includes a third element region, a third other-element region, and a third intermediate element region, the third element region is between a portion of the third conductive member and a portion of the fifth magnetic member in the first direction, the third other-element region is between the sixth magnetic member and an other portion of the third conductive member in the first direction, the third intermediate element region is between the third element region and the third other-element region in the second direction, the third intermediate element region overlaps a region between the fifth magnetic member and the sixth magnetic member in the first direction, the fifth magnetic member includes a ninth partial surface and a tenth partial surface, the ninth partial surface faces the third element region in the first direction, a position in the second direction of the ninth partial surface is between a position in the second direction of the tenth partial surface and a position in the second direction of the sixth magnetic member, a position in the first direction of the tenth partial surface is between a position in the first direction of the third conductive member and a position in the first direction of the ninth partial surface, the fourth element part further includes a seventh magnetic member and an eighth magnetic member, the eighth magnetic member is separated from the seventh magnetic member along the second direction, the fourth magnetic element includes a fourth magnetic layer, a fourth counter magnetic layer, and a fourth nonmagnetic layer provided between the fourth magnetic layer and the fourth counter magnetic layer, a direction from the fourth magnetic layer toward the fourth counter magnetic layer is along the first direction, the fourth magnetic element includes a fourth element region, a fourth other-element region, and a fourth intermediate element region, the fourth element region is between a portion of the fourth conductive member and a portion of the seventh magnetic member in the first direction, the fourth other-element region is between the eighth magnetic member and an other portion of the fourth conductive member in the first direction, the fourth intermediate element region is between the fourth element region and the fourth other-element region in the second direction, the fourth intermediate element region overlaps a region between the seventh magnetic member and the eighth magnetic member in the first direction, the seventh magnetic member includes a thirteenth partial surface and a fourteenth partial surface, the thirteenth partial surface faces the fourth element region in the first direction, a position in the second direction of the thirteenth partial surface is between a position in the second direction of the fourteenth partial surface and a position in the second direction of the eighth magnetic member, a position in the first direction of the fourteenth partial surface is between a position in the first direction of the fourth conductive member and a position in the first direction of the thirteenth partial surface.

Configuration 20

An inspection device, comprising:

the magnetic sensor according to any one of Configurations 1 to 19; and a processor processing an output signal obtained from the magnetic sensor.

According to embodiments, a magnetic sensor and an inspection device can be provided in which the sensitivity can be increased.

In the specification of the application, "perpendicular" and "parallel" refer to not only strictly perpendicular and strictly parallel but also include, for example, the fluctuation due to manufacturing processes, etc. It is sufficient to be substantially perpendicular and substantially parallel.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in magnetic sensors such as element parts, magnetic elements, magnetic layers, nonmagnetic layers, conductive members, circuits, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all magnetic sensors, and inspection devices practicable by an appropriate design modification by one skilled in the art based on the magnetic sensors, and the inspection devices described above as embodiments of the invention also are within the scope of the invention to the extent that the purport of the invention is included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A magnetic sensor, comprising:
    a first element part including
        a first magnetic element, the first magnetic element including a first magnetic layer, a first counter magnetic layer, and a first nonmagnetic layer provided between the first magnetic layer and the first counter magnetic layer, a direction from the first magnetic layer toward the first counter magnetic layer being along a first direction,
        a first conductive member,
        a first magnetic member, and
        a second magnetic member, the second magnetic member being separated from the first magnetic member along a second direction crossing the first direction,
    the first magnetic element including a first element region, a first other-element region, and a first intermediate element region,
    the first element region being between a portion of the first conductive member and a portion of the first magnetic member in the first direction,
    the first other-element region being between the second magnetic member and an other portion of the first conductive member in the first direction,
    the first intermediate element region being between the first element region and the first other-element region in the second direction,
    the first intermediate element region overlapping a region between the first magnetic member and the second magnetic member in the first direction,
    the first magnetic member including a first partial surface and a second partial surface,
    the first partial surface facing the first element region in the first direction,
    a position in the second direction of the first partial surface being between a position in the second direction of the second partial surface and a position in the second direction of the second magnetic member,
    a position in the first direction of the second partial surface being between a position in the first direction of the first conductive member and a position in the first direction of the first partial surface.

2. The magnetic sensor according to claim 1, wherein a portion of the first conductive member overlaps at least a portion of the second partial surface in the first direction.

3. The magnetic sensor according to claim 1, wherein
    the second magnetic member includes a third partial surface and a fourth partial surface,
    the third partial surface faces the first other-element region in the first direction,
    a position in the second direction of the third partial surface is between a position in the second direction of the first magnetic member and a position in the second direction of the fourth partial surface, and a position in the first direction of the fourth partial surface is between the position in the first direction of the first conductive member and a position in the first direction of the third partial surface.

4. The magnetic sensor according to claim 1, wherein the first magnetic member includes a first partial side surface between the first partial surface and the second partial surface, and the first partial side surface is oblique to the first partial surface.

5. The magnetic sensor according to claim 4, wherein an angle between the first partial side surface and the first partial surface is not less than 95 degrees and not more than 175 degrees.

6. The magnetic sensor according to claim 1, wherein a distance along the first direction between the position in the first direction of the first partial surface and the position in the first direction of the second partial surface is not less than 100 nm.

7. The magnetic sensor according to claim 1, wherein the first magnetic layer and the first counter magnetic layer include Fe and Co, and the first magnetic member and the second magnetic member include Fe, Co, and Ni.

8. The magnetic sensor according to claim 1, wherein the first element region includes a portion facing the first partial surface in the first direction, and a length along the second direction of the facing portion is not less than 0.1 times and not more than 0.9 times a length along the second direction of the first magnetic element.

9. The magnetic sensor according to claim 1, wherein the first magnetic element includes:
   a third-direction length along a third direction crossing a plane including the first and second directions; and
   a second-direction length along the second direction, and the third-direction length is greater than the second-direction length.

10. The magnetic sensor according to claim 9, further comprising:
   a first circuit,
   the first conductive member including a first conductive portion and a first other-conductive portion,
   a direction from the first conductive portion toward the first other-conductive portion being along the third direction,
   the first circuit being electrically connected to the first conductive portion and the first other-conductive portion, and being configured to supply a first current including an alternating current component between the first conductive portion and the first other-conductive portion.

11. The magnetic sensor according to claim 10, further comprising:
   a second circuit,
   the first magnetic element including a first element portion and a first other-element portion,
   a direction from the first element portion toward the first other-element portion being along the third direction,
   the second circuit being electrically connected to the first element portion and the first other-element portion, and being configured to supply a second current between the first element portion and the first other-element portion.

12. The magnetic sensor according to claim 9, further comprising:
   a second element part;
   a first resistance element;
   a second resistance element;
   a first circuit; and
   a second circuit,
   the second element part including a second magnetic element and a second conductive member,
   the first conductive member including a first conductive portion and a first other-conductive portion,
   the second conductive member including a second conductive portion and a second other-conductive portion,
   the first other-conductive portion being electrically connected to the second conductive portion,
   the first circuit being electrically connected to the first conductive portion and the second other-conductive portion, and being configured to supply a first current including an alternating current component between the first conductive portion and the second other-conductive portion,
   the first magnetic element including a first element portion and a first other-element portion,
   the second magnetic element including a second element portion and a second other-element portion,
   the first other-element portion being electrically connected to the second element portion,
   the first resistance element including a first resistance element portion and a first other-resistance element portion,
   the second resistance element including a second resistance element portion and a second other-resistance element portion,
   the first other-resistance element portion being electrically connected to the second resistance element portion,
   the first resistance element portion being electrically connected to the first element portion,
   the second other-resistance element portion being electrically connected to the second other-element portion,
   the second circuit being electrically connected to a first connection point and a second connection point,
   the first connection point being between the first other-element portion and the second element portion,
   the second connection point being between the first other-resistance element portion and the second resistance element portion,
   the second circuit being configured to supply a second current between the first connection point and the second connection point.

13. The magnetic sensor according to claim 12, wherein an orientation from the first conductive portion toward the first other-conductive portion is the same as an orientation from the first element portion toward the first other-element portion, and an orientation from the second conductive portion toward the second other-conductive portion is the same as an orientation from the second element portion toward the second other-element portion.

14. The magnetic sensor according to claim 12, further comprising:
   a third circuit,
   the third circuit being electrically connected to a third connection point and a fourth connection point,
   the third connection point being between the first resistance element portion and the first element portion, the fourth connection point being between the second other-resistance element portion and the second other-element portion, the third circuit being configured to detect a change of a potential between the third connection point and the fourth connection point.

15. The magnetic sensor according to claim 9, further comprising:

a second element part;
a third element part;
a fourth element part;
a first circuit; and
a second circuit, the second element part including a second magnetic element and a second conductive member, the third element part including a third magnetic element and a third conductive member, the fourth element part including a fourth magnetic element and a fourth conductive member, the first conductive member including a first conductive portion and a first other-conductive portion, the second conductive member including a second conductive portion and a second other-conductive portion, the third conductive member including a third conductive portion and a third other-conductive portion, the fourth conductive member including a fourth conductive portion and a fourth other-conductive portion, the first conductive portion being electrically connected to the third conductive portion, the second other-conductive portion being electrically connected to the fourth other-conductive portion, the first other-conductive portion being electrically connected to the second conductive portion, the third other-conductive portion being electrically connected to the fourth conductive portion, the first circuit being electrically connected to a first conductive connection point and a second conductive connection point, the first conductive connection point being between the first conductive portion and the third conductive portion, the second conductive connection point being between the second other-conductive portion and the fourth other-conductive portion, the first circuit being configured to supply a first current including an alternating current component between the first conductive connection point and the second conductive connection point, the first magnetic element including a first element portion and a first other-element portion, the second magnetic element including a second element portion and a second other-element portion, the third magnetic element including a third element portion and a third other-element portion, the fourth magnetic element including a fourth element portion and a fourth other-element portion, the first element portion being electrically connected to the third element portion, the second other-element portion being electrically connected to the fourth other-element portion, the first other-element portion being electrically connected to the second element portion, the third other-element portion being electrically connected to the fourth element portion, the second circuit being electrically connected to a first connection point and a second connection point, the first connection point being between the first other-element portion and the second element portion, the second connection point being between the third other-element portion and the fourth element portion, the second circuit being configured to supply a second current between the first connection point and the second connection point.

16. The magnetic sensor according to claim 15, wherein
an orientation from the first conductive portion toward the first other-conductive portion is the same as an orientation from the first element portion toward the first other-element portion, an orientation from the second conductive portion toward the second other-conductive portion is the same as an orientation from the second element portion toward the second other-element portion, an orientation from the third conductive portion toward the third other-conductive portion is the same as an orientation from the third element portion toward the third other-element portion, an orientation from the fourth conductive portion toward the fourth other-conductive portion is the same as an orientation from the fourth element portion toward the fourth other-element portion.

17. The magnetic sensor according to claim 15, wherein
a magnetic field due to the first current flowing in the first conductive member is applied to the first magnetic element,
a magnetic field due to the first current flowing in the second conductive member is applied to the second magnetic element,
a magnetic field due to the first current flowing in the third conductive member is applied to the third magnetic element, and
a magnetic field due to the first current flowing in the fourth conductive member is applied to the fourth magnetic element.

18. The magnetic sensor according to claim 15, further comprising:
a third circuit,
the third circuit being electrically connected to a third connection point and a fourth connection point,
the third connection point being between the first element portion and the third element portion,
the fourth connection point being between the second other-element portion and the fourth other-element portion,
the third circuit being configured to detect a change of a potential between the third connection point and the fourth connection point.

19. The magnetic sensor according to claim 15, wherein
the second element part further includes a third magnetic member and a fourth magnetic member,
the fourth magnetic member is separated from the third magnetic member along the second direction,
the second magnetic element includes a second magnetic layer, a second counter magnetic layer, and a second nonmagnetic layer provided between the second magnetic layer and the second counter magnetic layer,
a direction from the second magnetic layer toward the second counter magnetic layer is along the first direction,
the second magnetic element includes a second element region, a second other-element region, and a second intermediate element region, the second element region is between a portion of the second conductive member and a portion of the third magnetic member in the first direction, the second other-element region is between the fourth magnetic member and an other portion of the second conductive member in the first direction, the second intermediate element region is between the second element region and the second other-element region in the second direction, the second intermediate element region overlaps a region between the third magnetic member and the fourth magnetic member in the first direction, the third magnetic member includes a fifth partial surface and a sixth partial surface, the fifth partial surface faces the second element region in the first direction, a position in the second direction of the fifth partial surface is between a position in the second direction of the sixth partial surface and a position in the second direction of the fourth magnetic member, a position in the first direction of the sixth partial surface is between a position in the first direction of the second conductive member and a position in the first direction of the fifth partial surface, the third element part further includes a fifth magnetic member and a sixth magnetic member, the sixth magnetic member is separated from the fifth magnetic member along the second direction, the third magnetic element includes a third magnetic layer, a third counter magnetic layer, and a third nonmagnetic layer provided between the third magnetic layer and the third counter magnetic layer, a direction from the third magnetic layer toward the third counter magnetic layer is along the first direction, the third magnetic element includes a third element region, a third other-element region, and a third intermediate element region, the third element region is between a portion of the third conductive member and a portion of the fifth magnetic member in the first direction, the third other-element region is between the sixth magnetic member and an other portion of the third conductive member in the first direction, the third intermediate element region is between the third element region and the third other-element region in the second direction, the third intermediate element region overlaps a region between the fifth magnetic member and the sixth magnetic member in the first direction, the fifth magnetic member includes a ninth partial surface and a tenth partial surface, the ninth partial surface faces the third element region in the first direction, a position in the second direction of the ninth partial surface is between a position in the second direction of the tenth partial surface and a position in the second direction of the sixth magnetic member, a position in the first direction of the tenth partial surface is between a position in the first direction of the third conductive member and a position in the first direction of the ninth partial surface, the fourth element part further includes a seventh magnetic member and an eighth magnetic member, the eighth magnetic member is separated from the seventh magnetic member along the second direction, the fourth magnetic element includes a fourth magnetic layer, a fourth counter magnetic layer, and a fourth nonmagnetic layer provided between the fourth magnetic layer and the fourth counter magnetic layer, a direction from the fourth magnetic layer toward the fourth counter magnetic layer is along the first direction, the fourth magnetic element includes a fourth element region, a fourth other-element region, and a fourth intermediate element region, the fourth element region is between a portion of the fourth conductive member and a portion of the seventh magnetic member in the first direction, the fourth other-element region is between the eighth magnetic member and an other portion of the fourth conductive member in the first direction, the fourth intermediate element region is between the fourth element region and the fourth other-element region in the second direction, the fourth intermediate element region overlaps a region between the seventh magnetic member and the eighth magnetic member in the first direction, the seventh magnetic member includes a thirteenth partial surface and a fourteenth partial surface, the thirteenth partial surface faces the fourth element region in the first direction, a position in the second direction of the thirteenth partial surface is between a position in the second direction of the fourteenth partial surface and a position in the second direction of the eighth magnetic member, a position in the first direction of the fourteenth partial surface is between a position in the first direction of the fourth conductive member and a position in the first direction of the thirteenth partial surface.

20. An inspection device, comprising:

the magnetic sensor according to claim 1; and a processor processing an output signal obtained from the magnetic sensor.

* * * * *